United States Patent [19]

Bräunlich et al.

[11] Patent Number: 5,622,989

[45] Date of Patent: Apr. 22, 1997

[54] AMINO-BENZOFURYL-AND THIENYL-DERIVATIVES

[75] Inventors: Gabriele Bräunlich, Wuppertal; Rüdiger Fischer, Köln; Mazen Es-Sayed, Wuppertal; Rudolf Hanko, Düsseldorf, all of Germany; Stephen Tudhope, Windsor, Great Britain; Graham Sturton, Bray Maidenhead, Great Britain; Trevor Abram, Marlow, Great Britain; Wendy J. McDonald-Gibson, Wallingford, Great Britain; Mary F. Fitzgerald, Begbroke, Great Britain

[73] Assignee: Bayer Aktiengesellschaft, Leverkusen, Germany

[21] Appl. No.: 449,402

[22] Filed: May 23, 1995

[30] Foreign Application Priority Data

May 31, 1994 [GB] United Kingdom .................. 9410868
May 31, 1994 [GB] United Kingdom .................. 9410878
May 31, 1994 [GB] United Kingdom .................. 9410879

[51] Int. Cl.$^6$ ......................... A61K 31/34; C07D 307/80
[52] U.S. Cl. .......................... 514/469; 514/470; 549/466; 549/468; 546/281.7; 548/248
[58] Field of Search .................................. 549/468, 466; 546/281.7; 548/248; 514/469, 470

[56] References Cited

U.S. PATENT DOCUMENTS 5,120,742  6/1992  Rasmusson et al. ..................... 546/77

FOREIGN PATENT DOCUMENTS 0146243  6/1985  European Pat. Off. .
0551662  7/1993  European Pat. Off. .
0623607  11/1994 European Pat. Off. .
351639   12/1972 Sweden .

OTHER PUBLICATIONS

Kunchell et al., Chem. Ber., vol. 36, p. 1260–1262 (1903).

Sarhan, Egyptian, J. Pharm. Sci, vol. 33 (3–4), pp. 631–638 1992.

Chemical Abstracts, vol. 77, No. 23, abstract No. 151884g, (1972).

Chemical Abstracts, vol. 78, No. 25, abstract No. 159427b, (1973).

S. Nagata et al., Int. Arch. Allergy Immonol., vol. 97, pp. 194–199, (1992).

*Primary Examiner*—Bernard Dentz
*Attorney, Agent, or Firm*—Sprung Horn Kramer & Woods

[57] ABSTRACT

6-Amino-benzofuryl- and thienyl-derivatives can be prepared by reacting appropriate amino-substituted benzoyl phenols with appropriate substituted acetophenones and subsequent modification of the substituents. The compounds are useful for the treatment of actual and chronic inflammatory diseases, particularly of the airways and the gastrointestinal tract.

14 Claims, No Drawings

AMINO-BENZOFURYL-AND THIENYL-DERIVATIVES

The invention relates to amino-benzofuryl- and thienyl-derivatives, processes for their preparation and their use in medicaments.

It is known that the NADPH oxidase of phagocytes is the physiological source to the superoxide radical anion and reactive oxygen species derived therefrom which are important in the defense against pathogens. Uncontrolled formation leads to tissue damage in inflammatory processes. It is additionally known that elevation of phagocyte cyclic AMP leads to inhibition of oxygen radical production and that this cell function is more sensitive than others such as aggregation or enzyme release (cf. Inb. Arch. Allergy Immunol., vol. 97: pp 194–199, 1992).

Benzofuran- and benzothiophen derivatives having lipoxygenase-inhibiting action are described in the publication EP 146 243.

Surprisingly it was found that compounds given by the general formula (I) inhibited oxygen radical formation and elevated cellular cyclic AMP levels probably by inhibition of phagocyte phosphodiesterase activity.

The invention relates to amino-benzofuryl- and thienyl-derivatives of the general

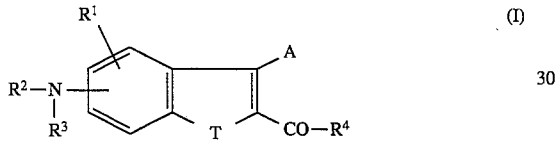

in which $R^1$ represents hydrogen or straight-chain or branched alkyl having up to 6 carbon atoms or represents halogen, carboxyl, cyano, nitro, trifluoromethyl or a group of a formula —$OR^5$, —$SR^6$ or —$NR^7R^8$, in which $R^5$, $R^6$ and $R^8$ are identical or different and denote hydrogen, cycloalkyl having 3 to 6 carbon atoms, benzyl or a 5 to 7-membered saturated or unsaturated heterocycle having up to 4 heteroatoms from the series comprising N, S and/or O and to which a phenyl ring can be fused and which is optionally substituted by identical or different substituents from the series comprising halogen, cyano, nitro or by a straight-chain or branched alkyl having up to 6 carbon atoms or denote straight-chain or branched alkyl or alkenyl each having up to 8 carbon atoms, or denote phenyl, which is optionally monosubstituted to disubstituted by identical or different substituents from the series comprising nitro, halogen, carboxy or straight-chain or branched alkoxycarbonyl having up to 6 carbon atoms, or $R^5$ denotes a hydroxyl protecting group, $R^7$ denotes hydrogen or a straight-chain or branched alkyl having up to 4 carbon atoms, $R^2$ represents formyl or straight-chain or branched acyl, alkoxy or alkoxycarbonyl each having up to 8 carbon atoms in the alkyl group, or represents benzoyl, which is optionally monosubstituted to trisubstituted by identical or different substituents from the series comprising halogen, cyano, carboxy, straight-chain or branched alkoxy, alkoxycarbonyl or acyl each having up to 6 carbon atoms in the alkyl group,

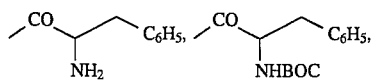

—$SO_2R^9$, —CO—$(CH_2)_a NR^{10}R^{11}$, —CO—$(CH_2)_b$—$R^{12}$, —CO—S—$R^{13}$ or a residue of the formula

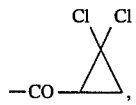

in which $R^9$ denotes straight-chain or branched alkyl having up to 6 carbon atoms, which is optionally substituted by phenyl, or denotes phenyl, which is optionally substituted by trifluoromethyl, cyano, nitro or straight-chain or branched alkyl having up to 6 carbon atoms, $R^{10}$ and $R^{11}$ are identical or different and denote hydrogen, straight-chain or branched alkyl having up to 6 carbon atoms or phenyl, $R^{12}$ denotes straight-chain or branched hydroxyl, oxyacyl, alloxy or alkoxycarbonyl each having up to 6 carbon atoms or carboxy, a denotes a number 0, 1, 2 or 3, b denotes a number 1, 2 or 3, $R^{13}$ denotes straight-chain or branched alkyl having up to 6 carbon atoms, $R^3$ represents hydrogen or straight-chain or branched alkyl having up to 6 carbon atoms, or has the above-mentioned meaning of $R^2$, T represents an oxygen or sulfur atom A represents hydrogen, hydroxyl, cycloalkyl with 3 to 6 carbon atoms, carboxy or straight-chain or branched alkoxycarbonyl or alkoxy each having up to 6 carbon atoms, or straight-chain or branched alkyl or alkenyl each having up to 8 carbon atoms and each of which is optionally mono-substituted by cyano or by a 5 to 7-membered saturated or unsaturated heterocycle having up to 4 heteroatoms from the series comprising N, S and O, which is optionally substituted by identical or different substituents from the series comprising hydroxy, halogen, cyano, nitro or by a straight-chain or branched alkyl having up to 6 carbon atoms, or alkyl or alkenyl are optionally substituted by a group of a formula

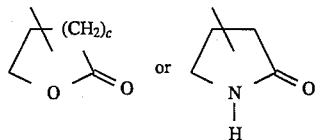

in which c denotes a number 1 or 2, and in which both rings are optionally monosubstituted by hydroxy, halogen or by straight-chain or branched alkyl having up to 6 carbon atoms, or alkyl or alkenyl are optionally monosubstituted by a group of a formula —CO—$R^{14}$, —CO—$NR^{15}R^{16}$, —$CONR^{17}$—$SO_2$—$R^{18}$ or —$PO(OR^{19})(OR^{20})$, —$OR^{21}$ or

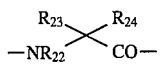

in which $R^{14}$ denotes hydroxyl, cycloalkyloxy having 3 to 7 carbon atoms or straight-chain or branched alkyl or alkoxy each having up to 8 carbon atoms, $R^{15}$, $R^{16}$ and $R^{17}$ are identical or different and represent hydrogen, straight-chain or branched alkyl having up to 6 carbon atoms, pheny or benzyl, or $R^{15}$ denotes hydrogen, and $R^{16}$ denotes hydroxyl, or $R^{15}$ and $R^{16}$ together with the nitrogen atom form a 5- or 6-membered saturated heterocycle, $R^{18}$ denotes a straight-chain or branched alkyl having up to 6 carbon atoms, which is optionally substituted by phenyl or trifluoromethyl, or denotes phenyl, which is optionally substituted by substituents from the series comprising halogen, cyano, nitro or by a straight-chain or branched alkyl having up to 6 carbon atoms, $R^{19}$, $R^{20}$ and $R^{21}$ are identical or different and represent hydrogen or straight-chain or branched alkyl having up to 6 carbon atoms, $R^{22}$ denotes hydrogen, an aminoprotecting group or straight-chain or branched alkyl having up to 6 carbon atoms, $R^{23}$ and $R^{24}$ are identical or different and denote hydrogen or straight-chain or branched alkyl having up to 4 carbon atoms, or $R^{23}$ has the abovementioned meaning, and $R^{24}$ denotes cycloalkyl having 3 to 6 carbon atoms or aryl having 6 to 10 carbon atoms or straight-chain or branched alkyl having up to 8 carbon atoms, which is optionally substituted by cyano, methylthio, hydroxy, mercapto, guanidyl or a group of a formula $-NR^{25}R^{26}$ or $R^{27}-CO-$, wherein $R^{25}$ and $R^{26}$ have the meaning shown above for $R^{15}$, $R^{16}$ and $R^{17}$, $R^{27}$ denotes hydroxyl, benzyloxycarbonyl, straight-chain or branched alkoxy having up to 6 carbon atoms or the above-mentioned group $-NR^{25}R^{26}$, or alkyl is optionally substituted by cycloalkyl having 3 to 6 carbon atoms, or by aryl having up to 10 carbon atoms, which is optionally substituted by hydroxyl, halogen, nitro, straight-chain or branched alkoxy having up to 8 carbon atoms or by the abovementioned group of the formula $-NR^{25}R^{26}$, or alkyl is optionally substituted by indolyl or by a 5 to 6 membered unsaturated heterocycle having up to 4 N-atoms wherein optionally all —NH-functions are protected by straight-chain or branched alkyl having up to 6 carbon atoms or by an amino protecting group, and $R^4$ represents phenyl, which is optionally monosubstituted to trisubstituted by identical or different substituents from the series comprising hydroxyl, adamantyl, phenoxy, cycloalkyl having up 3 to 6 carbon atoms, halogen, nitro, furanyl, thienyl, pyridyl, tetrazolyl, trifluoromethyl, difluoromethyl, cyano, carboxyl, straight-chain or branched alkyl, alkoxy, alkoxycarbonyl or acyl each having up to 11 carbon atoms in the alkyl group or by phenyl, which is optionally monosubstituted to tribsubstituted by nitro, halogen, formyl, carbonyl or straight chain or branched alkoxy, acyl, alkoxycarbonyl or alkyl each having up to 6 carbon atoms, which is optionally substituted by hydroxyl or phenyl is substituted by a group of formula $-NR^{28}R^{29}$, $-SR^{30}$, $SO_2R^{31}$, $-O-SO_2R^{32}$ or

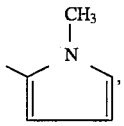

in which $R^{28}$ and $R^{29}$ have the meaning shown above for $R^{10}$ and $R^{11}$, or $R^{28}$ denotes hydrogen, and $R^{29}$ denotes straight-chain or branched acyl having up to 6 carbon atoms, $R^{30}$ denotes straight-chain or branched alkyl having up to 6 carbon atoms, $R^{31}$ and $R^{32}$ are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, with the proviso that A does not denote methyl or if A represents a methyl group $R^1$, T and $R^4$ have the meaning described in part I, and in this case $R^2$ and $R^3$ are identical or different and represent hydrogen or straight-chain or branched alkyl having up to 6 carbon atoms, or represent formyl or straight-chain or branched acyl, alkoxy or alkoxycarbonyl each having up to 8 carbon atoms, or represent benzoyl, which is optionally monosubstituted to trisubstituted by identical or different substituents from the series comprising halogen, cyano, carboxy, straight-chain or branched alkoxy, alkoxycarbonyl or acyl each having up to 6 carbon atoms, or represent a group of a formula $-SO_2(NH)_gR^{33}$, $SO_2NH_2$, $-CO-(CH_2)_dNR^{34}R^{35}$, $-(CH_2)_e-CO-R^{36}$, $-CO-(CH_2)_f-R^{37}$ or $-CO-X$, in which $R^{33}$ has the abovementioned meaning of $R^9$ and is identical or different to the latter, $R^{34}$ and $R^{35}$ are identical or different and have the abovementioned meaning of $R^{10}$ and $R^{11}$, $R^{36}$ denotes hydroxyl or straight-chain or branched alkoxy having up to 6 carbon atoms, $R^{37}$ has the abovementioned meaning of $R^{12}$ or denotes straight-chain or branched alkoxy or oxyacyl each having up to 6 carbon atoms or hydroxyl, d has the abovementioned meaning of a, e denotes a number 1, 2, 3, 4 or 5, f has the abovementioned meaning of b, g denotes a number 0 or 1, X denotes a 5-membered saturated or unsaturated heterocycle having up to 3 heteroatoms from the serie comprising N, S and/or O, which is optionally monosubstituted to trisubstituted by nitro, methyl or ethyl, or X denotes a residue of the formula

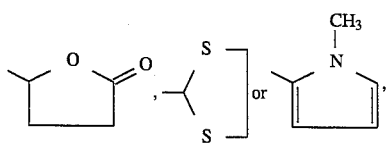

or

III

R¹, A and T have the meaning described in part I or

A represents methyl,

R² and R³ have the meaning described in part II, and in this case

R⁴ represents a 5 to 7 membered, saturated or unsaturated heterocycle, which can contain up to three oxygen, suphur and/or nitrogen atoms as heteroatoms and to which further a benzene ring can be fused and wherein both rings are optionally monosubstituted to trisubstituted by identical or different substituents from the series comprising hydroxyl, halogen, nitro, 1H-tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 8 carbon atoms or by a group of formula—NR³⁸R³⁹, —SR⁴⁰, SO₂R⁴¹ or —O—SO₂R⁴², in which R³⁸ and R³⁹ have the meaning shown above for R²⁸ and R²⁹ and are identical to the latter or different from the latter, R⁴⁰ has the abovementioned meaning of R³⁰, R⁴¹ and R⁴² are identical or different and have the abovementioned meaning of R³¹ and R³², and salts thereof.

The amino-benzofuryl- and thienyl-derivatives according to the invention can also be present in the form of their salts. In general, salts with organic or inorganic bases or acids may be mentioned here.

Physiologically acceptable salts are preferred in the context of the present invention. Physiologically acceptable salts of the amino-benzofuryl- and thienyl-derivatives can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Hydroxyl protective group in the context of the abovementioned definition in general represents a protective group from the series comprising: trimethylsilyl, tert.butyl-dimethylsilyl, benzyl, 4-nitrobenzyl, 4-methoxybenzyl, acetyl, tetrahydropyranyl and benzoyl.

Heterocycle in general represents a 5- to 7-membered, preferably 5- to 6-membered, saturated or unsaturated ring which can contain up to four oxygen, sulphur and/or nitrogen atoms as heteroatoms and to which further benzene ring can be fused.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, cinnolyl, thiazolyl benzothiaazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl or piperazinyl.

Preferred compounds of the general formula (I) are those in which

I

R¹ represents hydrogen, straight-chain or branched alkyl having up to 4 carbon atoms or represents fluorine, chlorine, bromine, nitro, trifluoromethyl or a group of a formula —OR⁵, —SR⁶ or —NR⁷R⁸, in which R⁷ denotes hydrogen or a straight-chain or branched alkyl having up to 3 carbon atoms, R⁵, R⁶ and R⁸ are identical or different and denote hydrogen, cyclopropyl, cyclopentyl, cyclohexyl, chinolyl, pyridyl, imidazolyl, 1,3-thiazolyl or thienyl, which are optionally substituted by identical or different substituents from the series comprising fluorine, chlorine, bromine, iodine, cyano, nitro or by a straight-chain or branched alkyl having up to 5 carbon atoms, or denote straight-chain or branched alkyl or alkenyl each having up to 6 carbon atoms, or denote phenyl, which is optionally monosubstituted to disubstituted by identical or different substituents from the series comprising nitro, fluorine, chlorine, bromine, iodine, carboxy or straight-chain or branched alkoxycarbonyl having up to 5 carbon atoms, or R⁵ denotes benzyl, acetyl or tetrahydropyranyl, R² represents formyl or straight-chain or branched acyl, alkoxy or alkoxycarbonyl each having up to 6 carbon atoms in the alkyl group, or represents benzoyl, which is optionally monosubstituted by substituents from the series comprising fluorine, chlorine, bromine, cyano, carboxy, straight-chain or branched alkoxy, alkoxycarbonyl or acyl each having up to 4 carbon atoms in the alkyl group, or represents a group of a formula

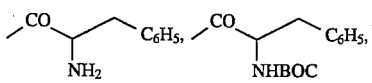

—SO₂R⁹, —CO—(CH₂)ₐNR¹⁰R¹¹, —CO—(CH₂)ᵦ—R¹², —CO—S—R¹³ or a residue of the formula

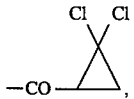

in which

R⁹ denotes straight-chain or branched alkyl having up to 4 carbon atoms, which is optionally substituted by phenyl, or denotes phenyl, which is optionally substituted by trifluoiomethyl, cyano, nitro or straight-chain or branched alkyl having up to 4 carbon atoms, R¹⁰ and R¹¹ are identical or different and denote hydrogen, straight-chain or branched alkyl having up to 4 carbon atoms or phenyl, R¹² denotes straight-chain or branched alkoxycarbonyl having up to 4 carbon atoms or carboxy, a denotes a number 0, 1, 2 or 3, b denotes a number 1, 2 or 3, R¹³ denotes straight-chain or branched alkyl having up to 4 carbon atoms, R³ represents hydrogen or straight-chain or branched alkyl having up to 4 carbon atoms, or has the abovementioned meaning of R², T represents an oxygen atom A represents hydrogen, hydroxyl, cyclopropyl, cyclobutyl, cyclopentyl, carboxyl or straight-chain or a branched alkoxycarbonyl or alkoxy each having up to 4 carbon atoms, or straight-chain or branched alkyl or alkenyl each having up to 6 carbon atoms and each of which is optionally monosubstituted by cyano, tetrazolyl, oxazolyl, oxazolinyl, thiazolyl or a group of formula

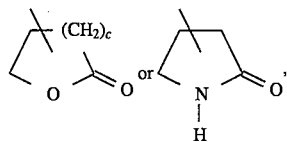

in which c denotes a number 1 or 2 and in which all rings are optionally monosubstituted by hydroxy, fluorine, bromine, chlorine or by straight-chain or branched alkyl having up to 4 carbon atoms, or alkyl or alkenyl are optionally monosubstituted by a group of a formula —CO—R¹⁴, —CO—NR¹⁵R¹⁶ or —OR²¹, in which R¹⁴ denotes hydroxyl, cyclopropyloxy, cyclopentyloxy, cyclohexyloxy or straight-chain or branched alkyl or alkoxy each having up to 6 carbon atoms, R¹⁵ and R¹⁶ are identical or different and represent hydrogen, straight-chain or branched alkyl having up to 4 carbon atoms, phenyl or benzyl, or R¹⁵ denotes hydrogen, and R¹⁶ denotes hydroxyl, or R¹⁵ and R¹⁶ together with the nitrogen atom form a pyrrolidinyl, morpholinyl or a piperidinyl ring, R²¹ represents hydrogen or straight-chain or branched alkyl having up to 6 carbon atoms, and R⁴ represents phenyl, which is optionally monosubstituted to trisubstituted by identical or different substituents from the series comprising hydroxyl, adamantyl, phenoxy, cyclopropyl, cyclopentyl, cyclohexyl, fluorine, chlorine, bromine, iodine, nitro, tetrazolyl, furanyl, thienyl, pyridyl, trifluoromethyl, difluoromethyl, cyano, carboxy, straight-chain or branched alkyl, alkoxy, alkoxycarbonyl or acyl each having up to 10 carbon atoms in the alkyl group, or by phenyl, which is optionally monosubstituted to tribsubstituted by fluorine, chlorine, bromine, nitro,
formyl or straight-chain or branched alkoxy, acyl, ethoxycarbonyl or alkyl each having up to 4 carbon atoms, which is optionally substituted by hydroxyl, or phenyl is substituted by a group of formula —NR²⁸R²⁹, —SR³⁰, —SO₂R³¹, —O—SO₂R³² or

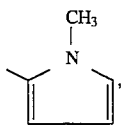

in which

R²⁸ and R²⁹ have the meaning shown above for R¹⁰ and R¹¹, or

R²⁸ denotes hydrogen, and

R²⁹ denotes straight-chain or branched acyl having up to 6 carbon atoms,

R³⁰ denotes straight-chain or branched alkyl having up to 4 carbon atoms,

R³¹ and R³² are identical or different and represent straight-chain or branched alkyl having up to 5 carbon atoms or phenyl, which is optionally substituted by trifluoromethyl, fluorine, chlorine, bromine or straight-chain or branched alkyl having up to 3 carbon atoms, with the proviso that A does not denote methyl, or

II if A represents a methyl group

R¹, T and R⁴ have the meaning described in part I, and in this case

R² and R³ are identical or different and represent hydrogen or straight-chain or branched alkyl having up to 4 carbon atoms, or represent formyl or straight-chain or branched acyl, or alkoxycarbonyl each having up to 4 carbon atoms, or represent benzoyl, which is optionally substituted by substituents from the series comprising fluorine, chlorine, bromine, cyano, carboxy, straight-chain or branched alkoxy, alkoxycarbonyl or acyl each having up to 4 carbon atoms, or represent a group of a formula —SO₂—(NH)₉—R³³, SO₂NH₂, —CO—(CH₂)_d—NR³⁴R³⁵, —(CH₂)_e—CO—R³⁶, —CO—(CH₂)_f—R³⁷ or CO—X, in which R³³ has the abovementioned meaning of R⁹ and is identical or different to the latter, R³⁴ and R³⁵ are identical or different and denote hydrogen or methyl, R³⁶ denotes hydroxyl or straight-chain or branched alkoxy having up to 4 carbon atoms or carboxy, R³⁷ has the abovementioned meaning of R¹² or denotes hydroxyl or straight-chain or branched alkoxy or oxacyl each having up to 4 carbon atoms, d has the abovementioned meaning of a, e denotes a number 1, 2, 3 or 4, f has the abovementioned meaning of c, g denotes a number 0 or 1, X denotes pyrrolyl, furyl or isoxazolyl, which are optionally mono-substituted to trisubstituted by nitro, methyl or ethyl or X denotes a residue of the formula

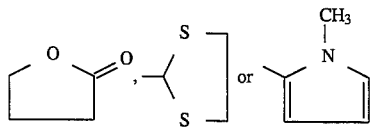

or

III $R^1$, A and T have the meaning described in part I, or

A represents methyl, $R^2$ and $R^3$ have the abovementioned meaning described in part II and in this case $R^4$ represents pyridyl, imidazolyl, pyrazolyl, thienyl, isothiazolyl, 1,3-thiazolyl or benzo[b]thiophenyl, where all rings are optionally monosubstituted to trisubstituted by identical or different substituents from the series comprising hydroxyl, fluorine, chlorine, bromine, iodine, nitro, 1H-tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 6 carbon atoms or by a group of formula $-NR^{38}R^{39}$, $-SR^{40}$, $-SO_2R^{41}$ or $-O-SO_2R^{42}$, in which $R^{38}$ and $R^{39}$ have the meaning shown above for $R^{28}$ and $R^{29}$ and are identical to the latter or different from the latter, $R^{40}$ has the abovementioned meaning of $R^{30}$, $R^{41}$ and $R^{42}$ are identical or different and have the abovementioned meaning of $R^{31}$ and $R^{32}$, and salts thereof.

Particularly preferred compounds of the general formula (I) are those in which

I $R^1$ represents hydrogen, straight-chain or branched alkyl having up to 3 carbon atoms, fluorine, chlorine, bromine, nitro or trifluoromethyl, $R^2$ represents formyl or straight-chain or branched acyl, or alkoxycarbonyl each having up to 5 carbon atoms in the alkyl group, or represents benzoyl, which is optionally substituted by substituents from the series comprising fluorine, chlorine, bromine, cyano, carboxy, straight-chain or branched alkoxy, alkoxycarbonyl or acyl, each having up to 3 carbon atoms in the alkyl group, or represents a group of a formula

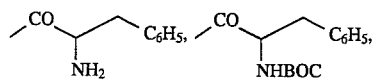

$-SO_2R^9$, $-CO-(CH_2)_aNR^{10}R^{11}$, $-CO-(CH_2)_b-R^{12}$, $-CO-S-R^{13}$ or a residue of the formula

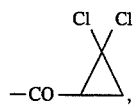

in which $R^9$ denotes straight-chain or branched alkyl having up to 4 carbon atoms, which is optionally substituted by phenyl, or denotes phenyl, which is optionally substituted by trifluoromethyl, cyano or straight-chain or branched alkyl having up to 3 carbon atoms, $R^{10}$ and $R^{11}$ are identical or different and denote hydrogen, straight-chain or branched alkyl having up to 3 carbon atoms or phenyl, $R^{12}$ denotes straight-chain or branched alkoxycarbonyl having up to 3 carbon atoms or carboxy, denotes a number 0, 1, 2 or 3, b denotes a number 1, 2 or 3, $R^{13}$ denotes straight-chain or branched alkyl having up to 3 carbon atoms, $R^3$ represents hydrogen or straight-chain or branched alkyl having up to 3 carbon atoms, or has the abovementioned meaning of $R^2$, T represents an oxygen or sulfur atom, A represents hydrogen, hydroxyl, cyclopropyl, cyclobutyl, cyclopentyl, carboxyl, or straight-chain or a branched alkoxycarbonyl or alkoxy each having up to 3 carbon atoms, or straight-chain or branched alkyl having up to 5 carbon atoms which is optionally monosubstituted by cyano or by a group of a formula $-CO-R^{14}$, $-CO-NR^{15}R^{16}$, in which $R^{14}$ denotes hydroxyl, cyclopropyloxy, cyclopentyloxy, cyclohexyloxy or straight-chain or branched alkyl or alkoxy having up to 5 carbon atoms, $R^{15}$ and $R^{16}$ are identical or different and denote hydrogen, straight-chain or branched alkyl having up to 3 carbon atoms or phenyl, and $R^4$ represents phenyl, which is optionally monosubstituted to trisubstituted by identical or different substituents from the series comprising hydroxyl, adamantyl, phenoxy, N-methyl-pyrrolyl, cyclopropyl, cyclopentyl, cyclohexyl, fluorine, chlorine, bromine, furanyl, thienyl, pyridyl, nitro, trifluoromethyl, difluoromethyl, cyano, carboxyl, methylthio, straight-chain or branched alkyl, alkoxy, acyl or alkoxycarbonyl each having up to 9 carbon atoms, or by phenyl, which is optionally monosubstituted to trisubstituted by fluorine, chlorine, bromine, nitro, formyl or straight-chain or branched alkoxy, alkoxycarbonyl, acyl or alkyl each having up to 4 carbon atoms, which is optionally substituted by hydroxyl, with the proviso that A does not denote methyl, or

II if A represents a methyl group, $R^1$, T and $R^4$ have the meaning described in part I, and in this case $R^2$ and $R^3$ are identical or different and represent hydrogen or straight-chain or branched alkyl having up to 3 carbon atoms, or represent formyl or straight-chain or branched acyl or alkoxycarbonyl each having up to 4 carbon atoms, or represent benzoyl, which is optionally substituted by substituents from the series comprising fluorine, chlorine, bromine, cyano, straight-chain or branched alkoxy or alkoxycarbonyl each having up to 3 carbon atoms, or represent a group of a formula $-CO-NH_2$, $-SO_2(NH)_gR^{37}$, $-SO_2NH_2$, $-(CH_2)_e-CO-R^{36}$, $-CO-(CH_2)_f-R^{37}$ or $-CO-X$, in which $R^{33}$ has the abovementioned meaning of $R^9$ and is identical or different to the latter, $R^{34}$ and $R^{35}$ are identical or different and denote hydrogen or methyl, $R^{37}$ has the abovementioned meaning of $R^{12}$ or denotes hydroxyl or straight-chain or branched alkoxy or oxacyl having up to 4 carbon atoms, $R^{36}$ denotes hydroxyl or straight-chain or branched alkoxy having up to 3 carbon atoms, d has the abovementioned meaning of a, e denotes a number 1, 2, 3 or 4, f has the abovementioned meaning of b, g denotes a number 0 or 1, X denotes pyrrolyl, N-methyl-pyrrolyl, furyl or isoxacolyl, which are optionally monosubstituted to trisubstituted by nitro, methyl or ethyl, X denotes a residue of the formula

[structure]

b denotes a number 1 or 2, or

III $R^1$, A and T have the abovementioned meaning described in part I, or

A represents methyl, in which $R^2$ and $R^3$ have the meaning described in part II, and in this case $R^4$ represents pyridyl, which optionally is up to substituted to trisubstituted by identical or different substituents from the series comprising hydroxyl, fluorine, chlorine, bromine, nitro, trifluoromethyl, trifluoromethoxy, difluoromethyl, difluoromethoxy, cyano, carboxy, straight-chain or branched alkyl, alkoxy, alkoxycarbonyl or acyl each having up to 5 carbon atoms, and salts thereof.

A process for the preparation of the compounds of the general formula (I) has additionally been found, characterized in that

[A] compounds of the general formula (II)

[structure (II)]

in which $R^1$ and T have the abovementioned meaning, and

E denotes straight-chain or branched acyl having up to 4 carbon atoms, preferably acetyl, and D represents —$(CH_2)_2$—$(C_1$-$C_4)$—alkoxycarbonyl, by reaction with compounds of the formula (III)

$R_4$—CO—$CH_2$—L    (III)

in which $R^4$ has the abovementioned meaning and

L represents a leaving group such as chlorine, bromine, tosylate or mesylate, in inert solvents in the presence of a base, firstly are converted into compounds of the general formula (Ia)

[structure (Ia)]

in which $R^1$, T, D and E have the abovementioned meaning, and then the compounds (Ia) are reacted with compounds of the formula (IV) or (IVa)

$R^2$—L'    $R^3$—L'
(IV)         (IVc)

in which $R^2$ and $R^3$ have the abovementioned meaning, and

L' has the abovementioned meaning of L and is identical or different to the latter, in inert solvents, if appropriate, in the presence of a base, and in the case of other radicals mentioned for the meaning of substituent A D is varied, if appropriate, by splitting off protecting groups, alkylation and/or hydrolysis, or

[B] and in the case of A=$CH_2$—CO—$R^{14}$ first compounds of the general formula (IIa)

[structure (IIa)]

in which

E, T and $R^1$ have the abovementioned meaning and

D' denotes halogen, preferably chlorine, are converted in the presence of NaAc and an alcohol, preferably ethanol, to compounds of the general formula (V)

[structure (V)]

in which $R^1$, E and T have the abovementioned meaning, then are reacted with compounds of the general formula (VI)

$R^{14}$—OC—$CH_2$ $P^{\oplus}Ph_3$ $Br^{\ominus}$    (VI)

in which $R^{14}$ has the abovementioned meaning to compounds of the general formula (VII)

[structure (VII)]

in which

E, $R^1$, T and $R^{14}$ have the abovementioned meaning, in inert solvents, and in a last step are reacted with compounds of the general formula (VIII)

$R^4$—CO—L'    (VIII)

in which
R[4] and L' has the abovementioned meaning, in the presence of 'SnCl$_4$, and
optionally followed by reacting with compounds of the general formulae (IV) or (IVa).
The process according to the invention can be illustrated by way of example by the following equations:
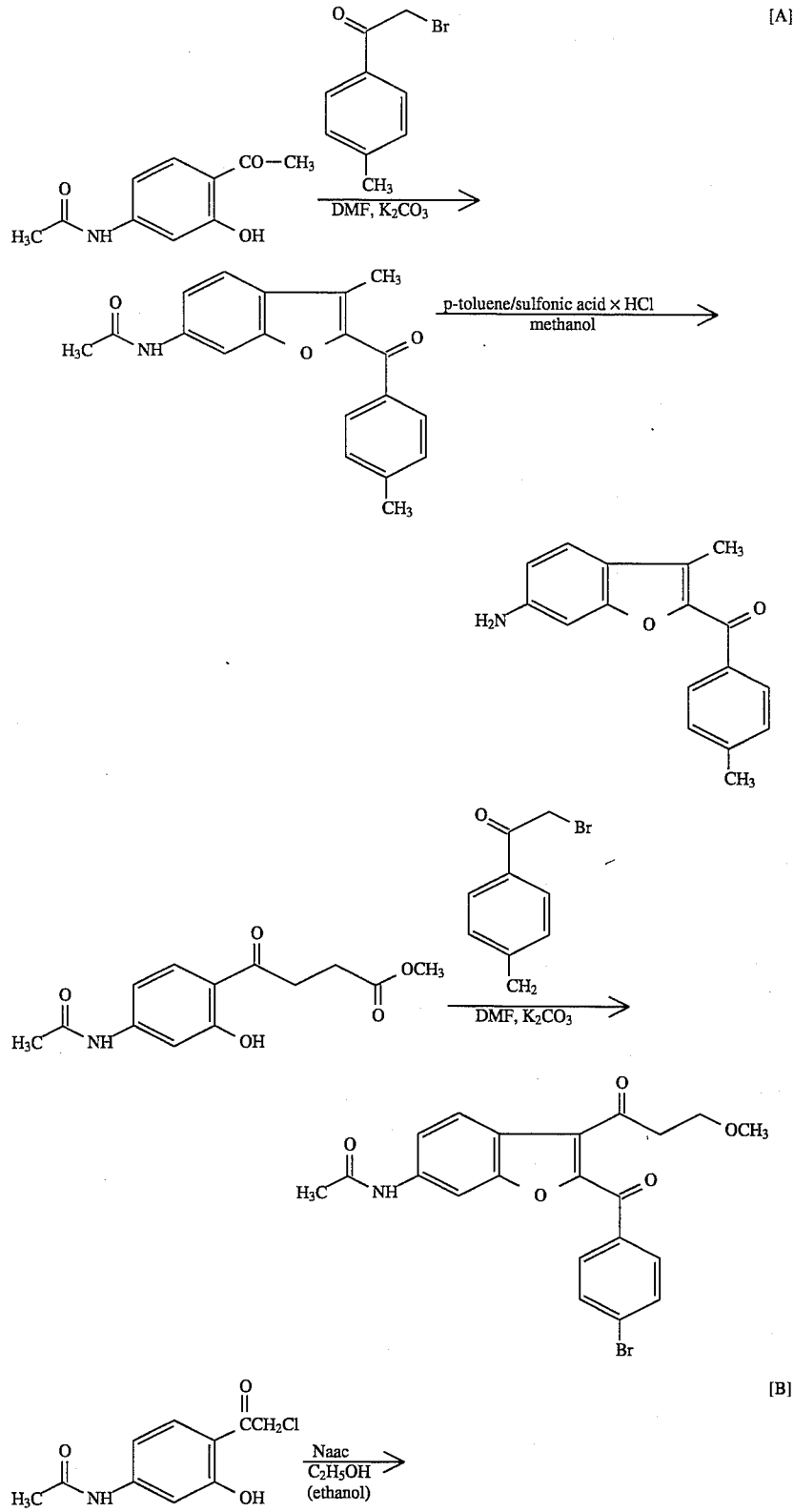

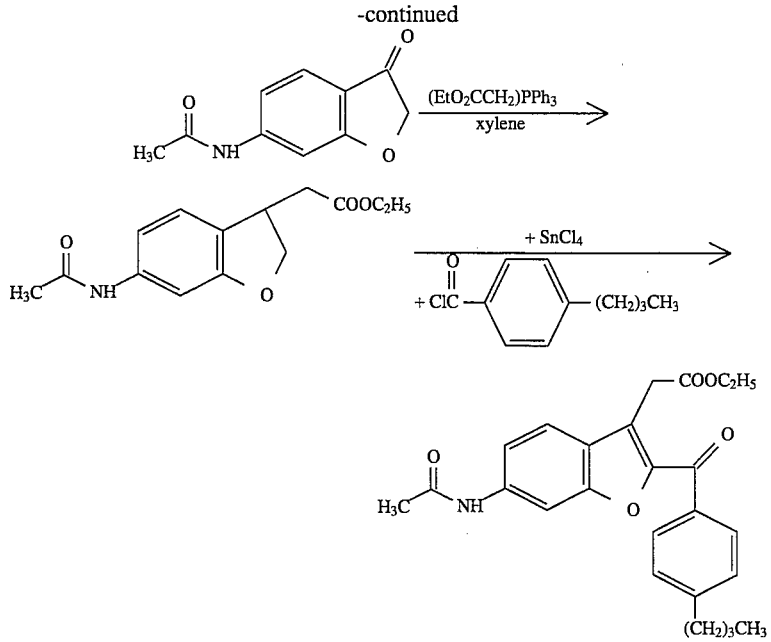

Suitable solvents are customary organic solvents which do not change under the reaction conditions. These include ethers such as diethyl ether, dioxane or tetrahydrofurane, acetone, dimethylsulfoxide, dimethylformamide or alcohols such as methanol, ethanol, propanol or halogenohydrocarbons such as dichlormethane, trichloromethane, tetrachloromethane or xylol. Methanol, dichloromethane and xylol are preferred.

Suitable bases generally are inorganic or organic bases. These preferably include alkali metal hydroxides such as, for example, sodium hydroxide, sodium hydrogencarbonate or potassium hydroxide; alkaline earth metal hydroxides such as, for example, barium hydroxide, alkali metal carbonates such as sodium carbonate, potassium carbonate, alkaline earth metal carbonates such as calcium carbonate, or alkaline metal oder alkaline earth metal alkoxides such as sodium methoxide or potassium methoxide, sodium ethoxide or potassium ethoxide or potassium tert.butoxide, or organic amines (trialkyl($C_1$–$C_6$)amines such as triethylamine, or heterocycles such as 1,4-diazabicyclo[2.2.2]octane (DABCO), 1,8-diazabicyclo[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodium-hydroxide are preferred.

The base is employed in an amount from 1 mol to 10 mol, preferably from 1.0 mol to 4 mol, relative to 1 mol of the compounds of the general formula (III).

The compounds of the general formula (Ia) are new and can be prepared as shown above.

The compounds of the general formula (II), (IIa), (III), (IV), (IVa), (V), (VI), (VII) and (VIII) are known or can be prepared by published methods.

The compounds according to the invention specifically inhibit the production of superoxide by polymorphonuclear leucocytes (PMN) without impairing other cell functions such as degranulation or aggregation. The inhibition was mediated by the elevation of cellular cAMP probably due to inhibition of the type IV phosphodiesterase responsible for its degradation They can therefore be employed in medicaments for controlling acute and chronic inflammatory processes.

The compounds according to the invention are preferably suitable for the treatment and prevention of acute and chronic inflammations of the airways, such as emphysema, alveolitis, shock lung, asthma, bronchitis, arteriosclerosis, arthrosis, inflammations of the gastro-intestinal tract and myocarditis. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test description

1. Preparation of human PMN

Blood was taken from healthy subjects by venous puncture and neutrophils were purified by dextran sedimentation and resuspended in the buffered medium.

2. Inhibition of FMLP-stimulated production of superoxide racidal anions.

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 μM, the DMSO concentration was 0.1% v/v in all wells. After addition of cytochalasin b (5 μg×ml$^{-1}$) the plate was incubated for 5 min at 37° C. Neutrophils were then stimulated by addition of $4 \times 10^{-8}$M FMLP and superoxide generation measured as superoxide dismutase inhibitable reduction of cytochrome C by monitoring the $OD_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - ((Rx - Rb))]}{((Ro - Rb))} \cdot 100$$

Rx=Rate of the well containing the compound according to the invention.

Ro=Rate in the control well.

Rb=Rate in the superoxide dismutase containing blank well.

TABLE A

| Example No. | % Inhibition at 10 μM | IC$_{50}$ [μM] |
|---|---|---|
| 21 | 90 | 0,42 |
| 24 | 68 | 0,6 |

3. Measurement of PMN cyclic AMP concentration

The compounds according to the invention were incubated with $3.7 \times 10^6$ PMN for 5 min at 37° C. before addition of $4 \times 10^{-8}$M FMLP. After 6 min protein was precipitated by the addition of 1% v/v conc. HCl in 96% v/v ethanol containing 0.1 mM EDTA. After centrifugation the ethanolic extracts were evaporated to dryness under $N_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

4. Assay of PMN phosphodiesterase

PMN suspensions ($10^7$ cells/ml) were sonicated for 6×10 sec on ice. Aliquots (100 μl) were incubated for 5 min at 37° C. with the compounds according to the invention or vehicle before the addition of $^3$H-cAMP (1 mM and 200 nCi per incubation). After 20 min the reaction was stopped by heating at 100° C. for 45 seconds. After cooling 100 mg of 5'-nucleotidase was added to each tube and the samples incubated for 15 min at 37° C. The conversion to $^3$H-adenosine was determined was ion-exhange chromatography on Dowex AG-1x (chloride form) followed by liquid scintillation counting. Percentage inhibition was determined by comparison to vehicle containing controls.

5. Effect of intravenously administered compounds on the FMLP-induced skin edema guinea pigs Guinea pigs (600–800 g) were anaesthetized with pentobarbitone sodium (40 mg/kg, i.p.) and injected (i.v.) with a 0.5 ml mixture of pentamine sky blue (5% W/V) and $^{125}$I-HSA (1 μli/animal). 10 minutes later 3 intradermal injections of FMLP (10 μg/site), 1 injection of histamine (1 μg/site) and 1 injection of vehicle (100 μl of 0.2% DMSO V/V in Hanks Buffered salt solution) were made on the left hand side of the animal (preinjection sites). 5 minutes later the drug (1 ml/kg) or the vehicle (50% PEG 400 V/V in distilled water, 1 mg/kg) was administered (i.v.). 10 minutes later an identical pattern of interadermal injections was made on the opposite flank of the animal (post-injection sites). These responses were allowed to develop for 15 minutes before the animal was sacrificed and a blood sample taken.

Skin sites and plasma samples were counted for 1 minute on a gamma counter an the degree of oedema calculated as μl plasma/skin site. Statistical analysis was done by a paired t-test on the mean of the 3 pre-injection site values of μl plasma obtained for FMLP/animal. The percentage inhibition of drug or vehicle was calculated as follow $$X \% = 1 - \frac{\overline{X} \, \mu l \, \text{plasma(post-injection site)}}{\overline{X} \, \mu l \, \text{plasma(pre-injection site)}} \times 100$$

6. Effect of orally administered compounds on the FMLP-induced skin oedema of guinea-pigs in vivo Test's p.o.

Guinea-pigs (600–800 g) were fasted overnight and orally treated with vehicle (1% Tylose w/v at 5 ml/kg) or drug (10 mg/kg; 2 mg/ml in 1% Tylose at 5 ml/kg) 40 minutes later the animals were anestized with pentobarbitone sodium (40 mg/kg, i.P.) and 0.6 ml of a mixture of pontamine sky blue (5% w/v)and $^{125}$I-HSA (1 μci/animal) was injected (i.v.). 90 minutes after oral pretreatment FMLP (50 μg/site) was injected (i.d.) at 4 different sites, histamine (1 μg/site) and vehicle (100 μl, 1% DMSO v/v in Hanks buffered salt solution) were both injected (i.d.) at 2 different sites.

The responses were allowed to develop for 30 minutes before the animal was sacrificed and a blood sample taken. Skin sites and plasma samples were counted for 1 minute on a gamma counter. The degree of oedema was calculated as μl plasma/skin site. Statistical analysis was carried out by a Mann-Whitney U-test on the mean of the 4 values of μl Plasma obtained for FMLP/animal.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large amounts, it is advisable to divide these into several individual doses over the course of the day.

| | Solvents |
|---|---|
| I | petrolether:ethylacetate 1:1 |
| II | petrolether:ethylacetate 5:1 |
| III | petrolether:ethylacetate 5:2 |
| IV | dichlormethane:methanol 95:5 |
| V | dichlormethane:methanol 5:1 |
| DMF | dimethylformamide |

Starting Compounds

EXAMPLE I

4-Acetamido-2-hydroxy-g-oxo-benzen-butanoic acid, methylester

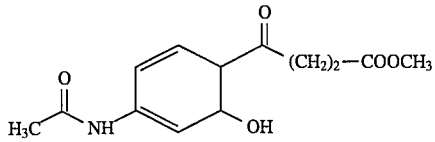

67.5 g (0.41 mol) 3-acetamidoanisol are suspended in 200 ml 1,2-dichloroethane and cooled in an ice bath. 217 g (1.64 mol) $AlCl_3$ and after it 73.9 g (0.49 mol) 3-carbomethoxypropionylchloride were added successively. Stirring was continued ½ hour. After 5 hours the reaction was quenched with ice and ethylacetate and water were added. The organic layer was seperated, washed with water, dried over $MgSO_4$ and concentrated in vacuo. The residue was recrystallized from dioxane and water.

Yield: 52 g (49% of theory)

EXAMPLE II

N-(4-Acetyl-3-hydroxy-phenyl)-acetamide

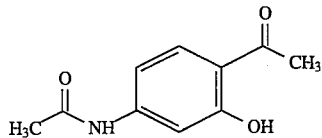

67.5 g (0.41 mol) 3-acetamidoanisol are suspended in 200 ml 1,2-dichloroethane and cooled in an ice bath. 217 g (1.64 mol) $AlCl_3$ and after it 38.5 g (0.49 mol) acetylchloride were added successively. Stirring was continued ½ hour. After 5 hours the reaction was quenched with ice and ethylacetate and water were added. The organic layer was seperated, washed with water, dried over $MgSO_4$ and concentrated in vacuo. The residue was recrystallized from dioxane and water.

Yield: 39 g (49% of theory)

EXAMPLE III

6-Acetylamido-2,3-dihydro-1-benzofuran-3-on

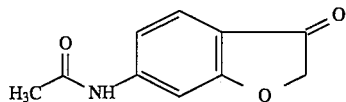

A solution of 10 g (43 mmol) 5-acetylamido-2-(2-chloroacetyl)-phenol and 12 g (140 mmol) sodium acetate in 125 ml ethanol was refluxed over night, cooled to room temperature, followed by addition of 300 ml $H_2O$. The ethanol was removed under reduced pressure and the residue cooled, filtered and dried. One obtained 8.5 g 6-acetylamido-2,3-dihydro-1-benzofuran-3-on, which was used for the next reaction without further purification.

$^1$H-NMR (200 MHz, $D_6$-DMSO): δ=2.11 (s, 3H), 4.76 (s, 2H), 7.12 (dd, 1H), 7.57 (d, 1H), 7.72 (d, 1H).

MSCCI): m/z (%)=192 (100) [$M^+$+1]

$R_f$=0.28 (PE/EE=1:1)

EXAMPLE IV

2-[3-(6-acetylamido-1-benzofuranyl)]ethyl acetate

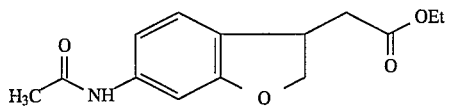

A suspension of 224 g (1.17 mmol) III and 490 g (1.4 mmol) (carbethoxymethylene)-triphenylphosphorane in 7.5 l xylene was refluxed over night. Another 389 g (1.17 mmol) (carbethoxymethylenemethylene)-triphenylphosphorane were added and the reaction mixture was refluxed for further 24 hours, concentrated under reduced pressure and the residue suspended in ether. The solids were filtered off and the organic phase concentrated in vacuo.

Purification of the crude followed by chromatography (PE/EA 1:1) yielding 115 g (38%) 2-[3-(6-acetylamido-1-benzofuranyl)]ethyl acetate.

$^1$H-NMR (250 MHz, $CDCl_3$): δ=1.26 (t, 3H), 2.20 (s, 3H), 3.66 (s, 2H), 4.18 (g, 2H), 7.13 (dd, 1H), 7.47 (d, 1H), 7.59 (s, 1H), 7.97 (d, 1H)

MSCCl, $NH_3$): m/z (%)=262 (100) [$M^+$+1]

$R_f$=0.19 (PE/EE=1:1).

Preparation Examples

EXAMPLE 1

3-[6-Acetamido-2-(4-chloro-benzoyl)-3-benzofuranyl]propanoic acid, methylester

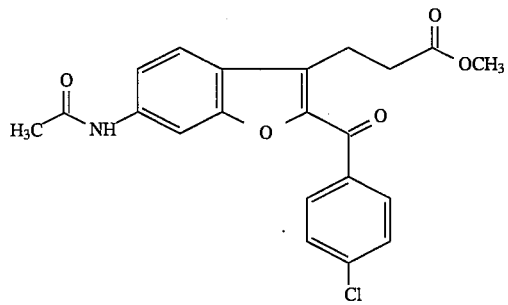

1.5 g (3.75 mmol) of 2'-Hydroxy-3-oxo-4'-[(acetamido)]benzenebutanoic acid, methylester and 1,13 g (4.1 mmol) of 2-bromo-4-chloroacetophenone were dissolved in 5 ml DMF and 1,55 g (11.25 mmol) of potassium carbonate were added. The suspension was heated to 60° C. for 1 h and ethylacetate was added. The organic phase was washed three times with water, one time with a NaCl solution, dried over $Na_2SO_4$ and concentrated in vacuo. The residue was further purified by crystallisation (ethanol).

Yield: 0.75 g (50%)

$R_f$=0,12 (III)

The compounds shown in Table 1 were prepared in analogy to the procedure of Example 1:

TABLE 1

| Ex.-No. | V | W | X | A | $R_f$* | Yield (% of theory) |
|---|---|---|---|---|---|---|
| 2 | Cl | H | Cl | COOC$_2$H$_5$ | 0,53 (IV) | 72 |
| 3 | H | H | F | CH$_2$CH$_2$COOCH$_3$ | 0,29 (I) | 28 |
| 4 | H | H | CN | CH$_2$CH$_2$COOCH$_3$ | 0,22 (I) | 46 |
| 5 | H | CH$_3$ | Cl | CH$_2$CH$_2$COOCH$_3$ | 0,23 (I) | 66 |
| 6 | H | H | SCH$_3$ | CH$_2$CH$_2$COOCH$_3$ | 0,31 (I) | 52 |
| 7 | H | Cl | H | CH$_2$CH$_2$COOCH$_3$ | 0,24 (I) | 58 |
| 8 | H | OCH$_3$ | H | CH$_2$CH$_2$COOCH$_3$ | 0,18 (I) | 68 |
| 9 | H | H | Cl | CO$_2$C$_2$H$_5$ | 0.4 (IV) | 20 |

EXAMPLE 10

N-[2-(4-Chloro-benzoyl)-3-(2-methoxycarbonyl-ethyl)-benzofuran-6-yl]-malonamic acid methyl ester

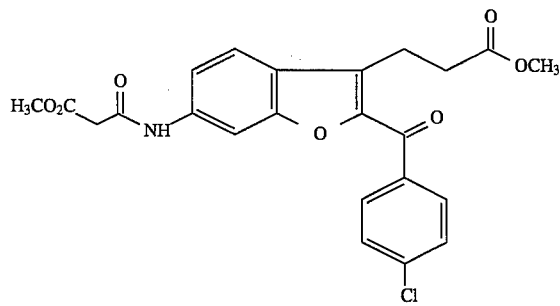

a)

3-[6-Amino-2-(4-chloro-benzoyl)-3-benzofuranyl] propanoic acid, methylester 3.1 g (7.7 mmol) of 2-(4-chloro-benzoyl)-6-acetamido-3-benzofuranylpropanoic acid methylester were suspended in 40 ml methanol. 20 ml 2.6N HCl were added with stirring. The reaction mixture was heated to reflux. After 1 hour a clear solution was obtained. After 3 hours reflux the solution was cooled to room temperature and ethylacetate was added. The organic layer was washed with NaOH-solution, two times with water, dried over Na$_2$SO$_4$ and concentrated in vacuo. The residue was further purified by crystallisation.

Yield: 2.26 g (82%)

$R_f$: 0.34 (III)

b)

0.5 g (1.4 mmol) of 3-[6-Amino-2-(4-chloro-benzoyl)-3-benzofuranyl]propanoic acid methylester were dissolved in 20 ml methylenechloride and 4 ml triethylamine(EtN$_3$). 0.6 g (4.5 mmol) (Cl—CO—CH$_2$—COOCH$_3$) methylmalonyl-chloride were added dropwise. The mixture was heated to reflux for 12 h. After removing the solvent, ethylacetate and water were added. The organic layer was washed twice with water and NaCl-solution, dried over Na$_2$SO$_4$ and concentrated in vacuo. The residue was further purified by recrystallisation (methanol).

Yield: 0.4 g (62.5%)

$R_f$ =0.88 (V)

The compounds shown in table 2 were prepared in analogy to the procedure of example 10:

TABLE 2

| Ex.-No. | W | X | A | R$^2$ | R$^3$ | $R_f$* | Yield (% of theory) |
|---|---|---|---|---|---|---|---|
| 11 | H | Cl | CH$_2$CH$_2$COOCH$_3$ | COCH$_2$CH$_2$COOCH$_3$ | H | 0.3 (III) | 61 |
| 12 | H | Cl | CH$_2$CH$_2$COOCH$_3$ | SO$_2$CH$_3$ | H | 0.58 (IV) | 12 |

TABLE 2-continued

[Structure: benzofuran with $R_2R_3N-$ at 6-position, A at 3-position, and 2-carbonyl-phenyl (with W at 3', X at 4') group]

| Ex.-No. | W | X | A | $R^2$ | $R^3$ | $R_f$* | Yield (% of theory) |
|---|---|---|---|---|---|---|---|
| 13 | H | Cl | $CH_2CH_2COOCH_3$ | $SO_2CH(CH_3)_2$ | H | 0,15 (III) | 14 |
| 14 | H | Cl | $CH_2CH_2CO_2CH_3$ | $SO_2C_2H_5$ | $SO_2C_2H_5$ | 0,1 (II) | 58 |
| 15 | H | Cl | $CH_2CH_2CO_2CH_3$ | $SO_2(CH_2)_2CH_3$ | H | 0,24 (III) | 18 |
| 16 | H | Cl | $CH_2CH_2CO_2CH_3$ | $SO_2-C_6H_5$ | $SO_2C_6H_5$ | 0,33 (III) | 88 |
| 17 | CN | H | $CH_2CH_2CO_2CH_3$ | $-CO-C(Cl)(Cl)$-cyclopropyl | H | 0,76 (I) | 70 |
| 18 | H | H | $CH_2CH_2CO_2CH_3$ | $-CO-S-C_2H_5$ | H | 0,75 (I) | 51 |

EXAMPLE 19

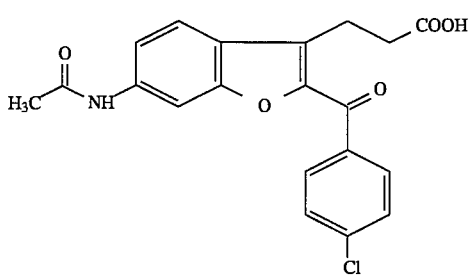

3-[6-Acetamido-2-(4-chlorobenzoyl)-3-benzofuranyl]propanoic acid 1.5 g (4.2 mmol) of the compound from starting compounds Example III were dissolved in 50 ml methanol/tetrahydrofuran (1:1) and 5.5 ml of a 2N NaOH solution were added. The mixture was stirred at r.t. for 24 hours, dissolved in water and acidified with 1N hydrochloric acid. The precipitate was filtered off, washed several times with water and dried in vacuo. The further reaction was carried out as described in Example 1.

Yield: 96%

$R_f$: 0,54 (V)

The compounds shown in Table 3 were prepared in analogy to the procedure of Example 19:

TABLE 3

[Structure: 6-acetamido-benzofuran with A at 3-position, 2-carbonyl-phenyl (V at 2', W at 3', X at 4')]

| Ex.-No. | V | W | X | A | $R_f$* | Yield (% of theory) |
|---|---|---|---|---|---|---|
| 20 | H | H | Cl | $CH_2CH_2CO_2Na$ | 0,58 (IV) | 98 |
| 21 | H | H | $SCH_3$ | $CH_2CH_2COOH$ | 0,68 (V) | 88 |
| 22 | H | H | F | $CH_2CH_2COOH$ | 0,51 (V) | 83 |
| 23 | H | Cl | H | $CH_2CH_2COOH$ | 0,51 (V) | 95 |
| 24 | H | $OCH_3$ | H | $CH_2CH_2COOH$ | 0,54 (V) | 87 |

EXAMPLE 25

3-[6-Acetamido-3-(2-carbonamid-ethyl)-2-(4-chloro-benzoyl)-benzofuran

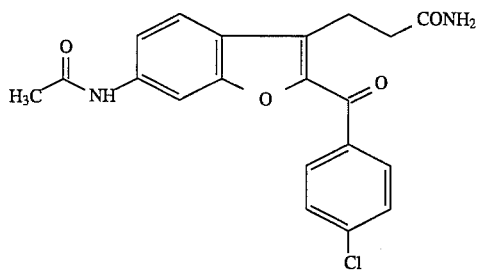

0.56 g (1.3 mmol) of the acid from example 1 were dissolved in 5 ml THF, 0.25 g (1.25 mmol) 1,1'-carbonyl-bis-1H-imidazole were added and the mixture was stirred at room temperature for 12 hours. Subsequently $NH_3$-gas was added for 2 h using an inlet pipe. After one additional hour stirring at r.t. the solvent was distilled off in vacuo. The residue was taken up in ethylacetate and washed three times with water, one time with a $NaHCO_3$ solution and one time with a NaCl solution. The organic phase was dried over $MgSO_4$ and the solvent was removed in vacuo.

Yield: 83%

$R_f$: 0,72 (V)

EXAMPLE 26

3-[6-Acetamido-2-(4-chloro-benzoyl)-3-(2-cyano-ethyl)-benzofuran

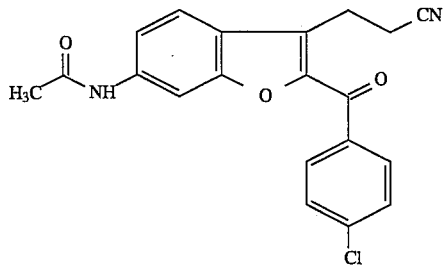

0.56 g (1.3 mmol) of example 25 were dissolved in 15 ml dioxane. 0.2 ml (2.6 mmol) pyridine were added, cooled to 5°–10° C. and 0.22 ml (1.56 mmol) trifluoroacetic anhydride were added dropwise. The mixture was stirred for 3 hours at room temperature. The mixture was added to water, washed twice with dichloromethane. The organic layer was dried and the solvent removed in vacuo.

Yield: 73%

$R_f$: 0,49 (IV)

The compounds shown in Table 4 were prepared in analogy to the procedure of Example 26:

TABLE 4

| Ex.-No. | $R^2$ | $R^3$ | $R_f$* | Yield (% of theory) |
|---|---|---|---|---|
| 27 | $CH_3SO_2-$ | H | 0,66 (IV) | 40 |
| 28 | $CH_3SO_2-$ | $CH_3SO_2-$ | 0,7 (IV) | 55 |

The compounds shown in Table 5 are prepared by Friedel-Crafts Reaction of Example IV.

TABLE 5

| Example No. | V | W | X | $R_f$* | yield (% of theory) |
|---|---|---|---|---|---|
| 29 | H | H | $-C_4H_9$ | 0.22 (I) | 31 |
| 30 | H | H | $-CH_3$ | 0.21 (I) | 86 |
| 31 | H | H | $-C_6H_5$ | 0.5 (IV) | 70 |
| 32 | Cl | H | $-Cl$ | 0.6 (IV) | 97 |
| 33 | H | H | $-Br$ | 0.25 (I) | 76 |
| 34 | H | Br | H | 0.33 (II) | 68 |
| 35 | H | CN | H | 0.25 (I) | 75 |

EXAMPLE 36

N-[3-Methyl-2-(4-methyl-benzoyl)-benzofuran-6-yl]acetamide

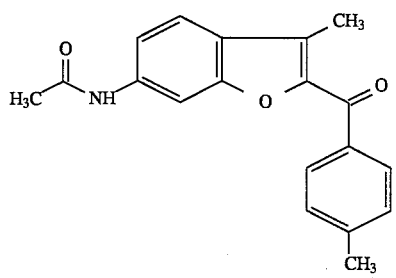

0.72 g (3.75 mmol) of N-(4-acetyl-3-hydroxy-phenyl)acetamide and 0.81 g (4.1 mmol) of 2-bromo-4-methylacetophenone were dissolved in 5 ml DMF and 1,55 g (11.25 mmol) of potassium carbonate were added. The suspension was heated to 60° C. for 1 h and ethylacetate was added. The organic phase was washed three times with water, one time with a NaCl solution, dried over $Na_2SO_4$ and concentrated in vacuo. The residue was further purified by crystallisation (ethanol).

Yield: 0.58 g (50%)

$R_f$=0,12 (III)

The compounds shown in Table 6 were prepared in analogy to the procedure of Example 36:

TABLE 6

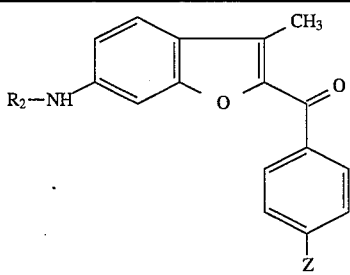

| Ex.-No. | Z | $R^2$ | $R_f$* | Yield (% of theory) |
|---|---|---|---|---|
| 37 | $CH_3$ | $CO_2CH_3$ | 0.64 (IV) | 87 |
| 38 | $CH_3$ | CHO | 0.91 (IV) | 64 |
| 39 | $CH_3$ | $CH_2CO_2C_2H_5$ | 0.69 (IV) | 20 |
| 40 | Cl | $COCH_3$ | 0.33 (IV) | 38 |
| 41 | $C_6H_5$ | $COCH_3$ | 0.35 (I) | 53 |

EXAMPLE 42

(6-Amino-3-methyl-benzofuran-2-yl)-(4-chlorophenyl)-methanone

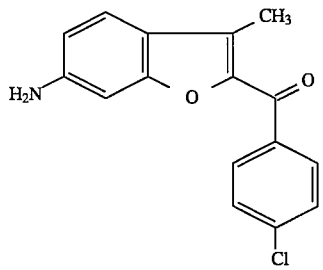

3.1 g (10 mmol) of N-[3-methyl-2-(4-methyl-benzoyl)benzofuran-6-yl]-acetamide were suspended in 40 ml methanol. 20 ml 2.6 N HCl were added with stirring. The reaction mixture was heated to reflux. After 1 hour a clear solution was obtained. After 3 hours reflux the solution was cooled to room temperature and ethylacetate was added. The organic layer was washed once with NaOH-solution, two times with water, dried over $Na_4SO_4$ and concentrated in vacuo. The residue was further purified by crystallisation.

Yield: 2,2 g (83%

$R_f$: 0.7 (IV)

The compounds shown in Tables 7 and 8 were prepared in analogy to the procedure of example 42:

TABLE 7

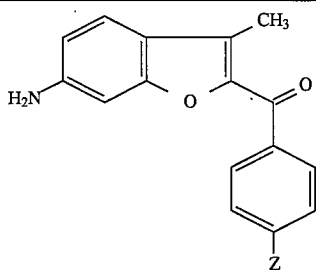

| Ex.-No. | Z | $R_f$* | Yield (% of theroy) |
|---|---|---|---|
| 43 | $CH_3$ | 0.62 (IV) | 87 |
| 44 | $C_6H_5$ | 0.38 | 71 |

TABLE 8

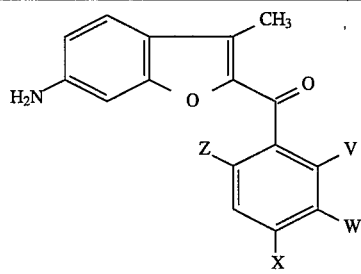

| Example No. | X | V | Z | W | $R_f$ | yield |
|---|---|---|---|---|---|---|
| 45 | $CH_3$ | $CH_3$ | $CH_3$ | H | 0.98 (IV) | 70 |
| 46 | Br | H | H | H | 0.45 (I) | 55 |
| 47 | $NO_2$ | H | H | H | 0.83 (I) | 22 |
| 48 | H | H | H | CN | 0.38 (IV) | 92 |
| 49 | CN | H | H | H | 0.77 (I) | 70 |

TABLE 8-continued

[Structure: 6-amino-3-methylbenzofuran-2-yl ketone with substituted phenyl ring bearing V, W, X, Z]

| Example No. | X | V | Z | W | R_f | yield |
|---|---|---|---|---|---|---|
| 50 | Cl | Cl | H | H | 0.26 (I) | 65 |
| 51 | H | H | H | NO$_2$ | 0.79 (I) | 88 |
| 52 | H | H | H | Br | 0.27 (I) | 71 |
| 53 | H | H | H | OCH$_3$ | 0.21 (I) | 96 |
| 54 | H | H | H | CH$_3$ | 0.25 (I) | 73 |
| 55 | H | H | H | CF$_3$ | 0.35 (I) | 37 |
| 56 | —C$_6$H$_4$—OCH$_3$ | H | H | NO$_2$ | 0.37 (II) | 40 |

The compounds shown in Table 9 were prepared in analogy to the procedure of example 36

TABLE 9

[Structure: R$_2$NH-substituted benzofuran with A group and substituted phenyl ketone bearing Y, W, Z]

| Example No. | Y | Z | W | R$^2$ | A | R_f | yield |
|---|---|---|---|---|---|---|---|
| 57 | H | C$_6$H$_5$ | H | CONH$_2$ | CH$_3$ | 0.18 (I) | 76 |
| 58 | H | NO$_2$ | H | COCH$_3$ | CH$_3$ | 0.28 (I) | 63 |
| 59 | H | Br | H | COCH$_3$ | CH$_3$ | 0.32 (I) | 73 |
| 60 | H | H | CN | COCH$_3$ | CH$_3$ | 0.47 (IV) | 29 |
| 61 | H | CN | H | COCH$_3$ | CH$_3$ | 0.27 (I) | 13 |
| 62 | Cl | Cl | H | COCH$_3$ | CH$_3$ | 0.4 (I) | 46 |
| 63 | H | H | NO$_2$ | COCH$_3$ | CH$_3$ | 0.29 (I) | 16 |
| 64 | H | H | Br | COCH$_3$ | CH$_3$ | 0.37 (I) | 43 |
| 65 | H | H | OCH$_3$ | COCH$_3$ | CH$_3$ | 0.29 (I) | 76 |
| 66 | H | H | CH$_3$ | COCH$_3$ | CH$_3$ | 0.13 (III) | 58 |
| 67 | H | H | CF$_3$ | COCH$_3$ | CH$_3$ | 0.13 (III) | 35 |
| 68 | H | —C$_6$H$_4$—OCH$_3$ | NO$_2$ | COCH$_3$ | CH$_3$ | 0.24 (I) | 7 |
| 69 | H | CH$_3$ | H | CO-(3-furyl) | CH$_3$ | 0.18 (III) | 30 |
| 70 | H | CH$_3$ | H | CO-(2-furyl) | CH$_3$ | 0.22 (III) | 35 |

TABLE 9-continued

| Example No. | Y | Z | W | R² | A | R_f | yield |
|---|---|---|---|---|---|---|---|
| 71 | H | CH₃ | H | CO-O-furan-NO₂ | CH₃ | 0.08 (II) | 40 |
| 72 | H | CH₃ | H | CO-(dihydrofuran-2,5-dione) | CH₃ | 0.02 (III) | 42 |
| 73 | H | CH₃ | H | CO-isoxazole | CH₃ | 0.12 (III) | 30 |
| 74 | H | CH₃ | H | CO-(3-methyl-furan) | CH₃ | 0.26 (II) | 35 |
| 75 | H | CH₃ | H | CO-(3-methylfuran) | CH₃ | 0.26 (III) | 40 |
| 76 | H | CH₃ | H | CO-(dimethyl-isoxazole) | CH₃ | 0.12 (III) | 30 |
| 77 | H | CH₃ | H | CO-(N-methylpyrrole) | CH₃ | 0.26 (II) | 35 |

EXAMPLE 78

3-[6-Acetylamino-2-(pyridine-4-carbonyl)-3-benzofuranyl]propanoic acid, methylester

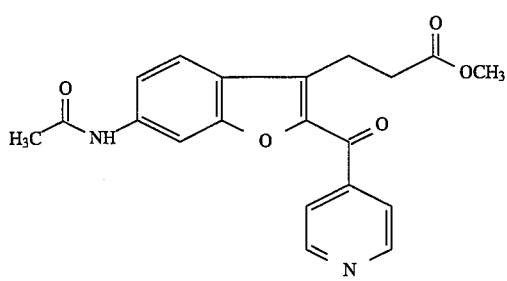

1.5 g (3.75 mmol) of 2'-Hydroxy-3-oxo-4'-[(acetamido)] benzenebutanoic acid, methylester and 0.82 g (4.1 mmol) of 2-bromo-1-(4-pyridyl)-ethanone were dissolved in 5 ml DMF and 1,55 g (11.25 mmol) of potassium carbonate were added. The suspension was heated to 50° C. for 1 h, ethylacetate was added. The organic phase was washed three times with water, one time with a NaCl solution, dried over $Na_2SO_4$ and concentrated in vacuo. The residue was further purified by chromatography.

Yield: 0.412 g (30%)

$R_f$=0,1, (I)

The compounds shown in Table 10 were prepared in analogy to the procedure of Example 78:

TABLE 10

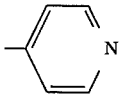

| Ex.-No. | A | R⁴ | $R_f$* | Yield (% of theory) |
|---|---|---|---|---|
| 79 | —COOC$_2$H$_5$ | 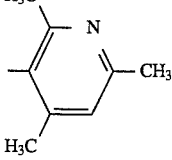 | 0,1 (I) | 30 |
| 80 | —CH$_2$CH$_2$CO$_2$CH$_3$ | 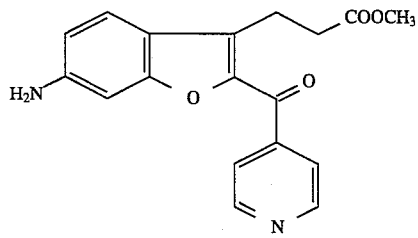 | 0,32 (IV) | 72 |

EXAMPLE 81

3-[6-Amino-2-(chloro-4-benzoyl)-3-benzofuranyl] propanoic acid, methylester

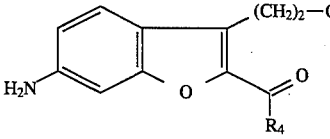

2.8 g (7.7 mmol) of 2-(4-chloro-benzoyl)-6-acetamido-3-benzofuranpropanoic acid methylester were suspended in 40 ml methanol. 20 ml 2.6 N HCl was added with stirring. The reaction mixture was heated to reflux. After 1 hour a clear solution was obtained. After 3 hours reflux the solution was cooled to room temperature and ethylacetate added. The organic layer was washed with NaOH-solution, two times with water, dried with Na$_2$SO$_4$ and concentrated in vacuo. The residue was further purified by crystallisation.

Yield: 1.64 g (60%)

$R_f$: 0.34 (III)

The compounds shown in Table 11 were prepared in analogy to the procedure of example 81:

TABLE 11

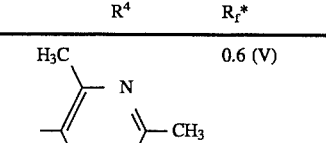

| Ex.-No. | R⁴ | $R_f$* | Yield (% of theory) |
|---|---|---|---|
| 82 | 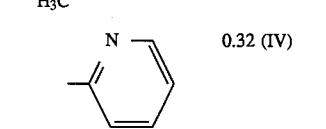 | 0.6 (V) | 90 |
| 83 | 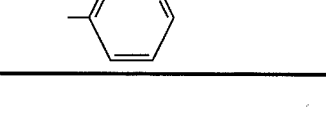 | 0.32 (IV) | 50 |
| 84 |  | 0.4 (IV) | 75 |

The compounds shown in Table 12 were prepared in analogy to the procedure of example 78.

TABLE 12

[Structure: benzofuran with H₃C—OC—HN substituent, A at 3-position, C(=O)R⁴ at 2-position]

| Example No. | A | R⁴ | R_f* | yield |
|---|---|---|---|---|
| 85 | C₂H₄COOCH₃ | 2-pyridyl | 0.25 (IV) | 30 |
| 86 | C₂H₄COOCH₃ | 3-pyridyl | 0.3 (IV) | 20 |
| 87 | CH₃ | 2,4,6-trimethylpyridyl | 0.34 (IV) | 63 |

The compounds shown in the Tables 13 and 14 are prepared in analogy to the procedure of 42.

TABLE 13

[Structure: benzofuran with NH₂ substituent, CH₃ at 3-position, C(=O)-phenyl(V,W,X) at 2-position]

| Example No. | V | W | X | R_f* | yield (% of theory) |
|---|---|---|---|---|---|
| 88 | H | H | F | 0.5 (I) | 98 |
| 89 | H | H | Br | 0.5 (III) | 97 |
| 90 | H | H | C₂H₅ | 0.44 (I) | 82 |
| 91 | H | H | cyclohexyl | 0.5 (I) | 82 |
| 92 | Cl | H | Cl | 0.63 (I) | 80 |
| 93 | H | NO₂ | H | 0.5 (I) | 70 |
| 94 | H | CH₃ | H | 0.63 (I) | 94 |
| 95 | CH₃ | H | CH₃ | 0.91 (I) | 81 |
| 96 | H | H | NO₂ | 0.83 (I) | 77 |
| 97 | H | CF₃ | H | 0.69 (I) | 91 |
| 98 | H | OCH₃ | H | 0.66 (I) | 90 |
| 99 | H | 4-methoxyphenyl | H | 0.42 (I) | 94 |

TABLE 14
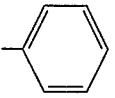
| Ex. No. | V | W | X | Z | $R_f$* | yield (% of theory) |
|---|---|---|---|---|---|---|
| 100 | H | 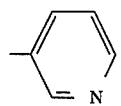 | H | H | 0.63 (I) | 100 |
| 101 | H | H | $C_9H_{19}$ | H | 0.84 (V) | 78 |
| 102 | H | H | $C_6H_{13}$ | H | 0.80 (V) | 76 |
| 103 | H | H | 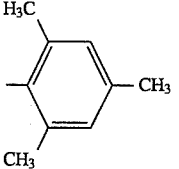 | H | 0.7 (V) | 97 |
| 104 | H | 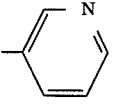 | H | H | 0.66 (III) | 93 |
| 105 | H | 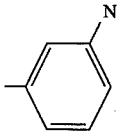 | H | H | 0.72 (III) | 78 |
| 106 | H | 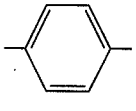 | H | H | 0.85 (V) | 95 |
| 107 | H | 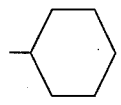 | H | H | 0.87 (V) | 100 |
| 108 | H | H | COOH | H | | |
| 109 | H | H | F | H | 0.77 (IV) | 77 |
| 110 | H | H | $C_2H_5$ | H | 0.84 (IV) | 78 |
| 111 | H | H | 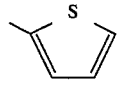 | H | 0.9 (IV) | 65 |
| 112 | H | H | $OCH_3$ | H | 0.371 (I) | 92 |
| 113 | $OCH_3$ | H | $OCH_3$ | H | 0.257 | 88.3 |
| 114 | H | H | OH | H | 0.27 (IV) | 43 |
| 115 | H | H |  | H | 0.85 (IV) | 80 |
| 116 | H | H | $NO_2$ | H | 0.79 (I) | 88 |
| 117 | H | H | Br | H | 0.78 (I) | 58 |
| 118 | H | H | $OCH_3$ | H | 0.75 (I) | 93 |
| 119 | Cl | Cl | H | H | 0.79 (I) | 40 |
| 120 | H | H | $CH_3$ | H | 0.34 (I) | 76 |

TABLE 14-continued

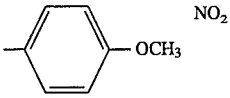

| Ex. No. | V | W | X | Z | $R_f^*$ | yield (% of theory) |
|---|---|---|---|---|---|---|
| 121 | H | H | CF$_3$ | H | 0.41 (I) | 97 |
| 122 | H | —C$_6$H$_4$—OCH$_3$ | NO$_2$ | H | 0.53 (I) | 40 |
| 123 | CH$_3$ | CH$_3$ | H | H | 0.98 (I) | 91 |
| 124 | H | —C$_6$H$_4$—C(O)OCH$_3$ | H | H | 0.53 (I) | 19 |
| 125 | H | H | —O—C$_6$H$_5$ | H | 0.72 (I) | 78 |

The compounds shown in Tables 15, 16, 17, 18, 19 and 20 are prepared in analogy to the procedure of example 1. Compounds with ethylacetate substituted in position A are prepared by Friedel-Crafts reaction of Example IV with aryl acid chloride.

TABLE 15

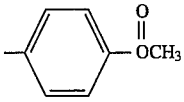

| Example No. | V | W | X | Z | A | $R_f^*$ | yield (% of theory) |
|---|---|---|---|---|---|---|---|
| 126 | H | H | CH$_3$ | H | cyclopropyl | 0.59 (IV) | 15 |
| 127 | H | CN | H | H | cyclopropyl | 0.5 (IV) | 76 |
| 128 | H | H | F | H | cyclobutyl | 0.46 (I) | 70 |
| 129 | H | H | cyclohexyl | H | cyclobutyl | 0.52 (I) | 87 |

TABLE 15-continued

| Example No. | V | W | X | Z | A | $R_f$* | yield (% of theory) |
|---|---|---|---|---|---|---|---|
| 130 | H | H | cyclohexyl | H | cyclopropyl | 0.55 (I) | 100 |
| 131 | H | H | F | H | cyclopropyl | 0.5 (I) | 89 |
| 132 | H | H | NO$_2$ | H | CH(CH$_3$)$_2$ | 0.5 (I) | 30 |
| 133 | H | H | CH$_3$ | H | CH(CH$_3$)$_2$ | 0.5 (I) | 77 |
| 134 | H | OCH$_3$ | H | H | CH(CH$_3$)$_2$ | 0.5 (I) | 65 |
| 135 | Cl | H | Cl | H | CH(CH$_3$)$_2$ | 0.53 (I) | 68 |
| 136 | CH$_3$ | H | CH$_3$ | H | CH(CH$_3$)$_2$ | 0.53 (I) | 86 |
| 137 | H | H | CF$_3$ | H | CH(CH$_3$)$_2$ | 0.53 (I) | 63 |
| 138 | H | H | CH$_3$ | H | cyclopropyl | 0.41 (I) | 61 |
| 139 | H | Br | H | H | OH | 0.69 (IV) | 25 |
| 140 | H | —OCH$_3$ | H | H | cyclobutyl | 0.48 (I) | 57 |
| 141 | H | H | CH$_3$ | H | —OH | 0.53 (V) | 52 |
| 142 | H | H | CH$_3$ | H | H | 0.21 (I) | 59 |
| 143 | H | —OCH$_3$ | H | H | —C$_2$H$_5$ | 0.37 (III) | 44 |
| 144 | H | —OCH$_3$ | H | H | cyclopropyl | 0.42 (I) | 51 |
| 145 | H | H | CH$_3$ | H | —OC$_2$H$_5$ | 0.43 (I) | 31 |
| 146 | H | CF$_3$ | H | H | cyclobutyl | 0.55 (I) | 68 |
| 147 | Cl | H | Cl | H | cyclobutyl | 0.54 (I) | 57 |
| 148 | H | CF$_3$ | H | H | cyclopropyl | 0.41 (I) | 65 |
| 149 | H | Br | H | H | cyclopropyl | 0.44 (I) | 72 |
| 150 | Cl | H | Cl | H | cyclopropyl | 0.62 (I) | 46 |
| 151 | H | CH$_3$ | H | H | —C$_2$H$_5$ | 0.51 (I) | 54 |
| 152 | H | CH$_3$ | H | H | cyclobutyl | 0.53 (I) | 77 |
| 153 | H | H | Cl | H | CH$_2$CO$_2$Et | 0.46 (V) | 44 |
| 154 | H | H | OCH$_3$ | H | CH(CH$_3$)$_2$ | 0.08 (III) | 79 |
| 155 | —OCH$_3$ | H | OCH$_3$ | H | CH(CH$_3$)$_2$ | 0.08 (III) | 83 |
| 156 | OCH$_3$ | H | OCH$_3$ | H | cyclopropyl | 0.13 (I) | 48.5 |

TABLE 15-continued

| Example No. | V | W | X | Z | A | R_f* | yield (% of theory) |
|---|---|---|---|---|---|---|---|
| 157 | H | H | OCH$_3$ | H | cyclopropyl | 0.26 (I) | 49.1 |
| 158 | H | H | Br | H | cyclopropyl | 0.28 (I) | 13 |
| 159 | H | H | phenyl | H | cyclopropyl | 0.44 (I) | 31 |
| 160 | H | Br | H | H | C$_2$H$_5$ | 0.3 (III) | 27 |
| 161 | H | H | CN | H | C$_2$H$_5$ | 0.6 (IV) | 45 |
| 162 | H | CN | H | H | C$_2$H$_5$ | 0.6 (IV) | 26 |
| 163 | H | H | C$_2$H$_5$ | H | C$_2$H$_5$ | 0.67 (IV) | 58 |
| 164 | H | H | cyclohexyl | H | C$_2$H$_5$ | 0.44 (I) | 74 |
| 165 | H | H | F | H | C$_2$H$_5$ | 0.07 (III) | 65 |
| 166 | H | H | Br | H | CH(CH$_3$)$_2$ | 0.3 (I) | 67 |
| 167 | H | Br | H | H | CH(CH$_3$) | 0.32 (I) | 31 |
| 168 | H | H | CN | H | CH(CH$_3$) | 0.65 (IV) | 38 |
| 169 | H | CN | H | H | CH(CH$_3$)$_2$ | 0.63 (IV) | 59 |
| 170 | H | H | C$_2$H$_5$ | H | CH(CH$_3$)$_2$ | 0.2 (III) | 88 |
| 171 | H | H | cyclohexyl | H | CH(CH$_3$)$_2$ | 0.2 (III) | 75 |
| 172 | H | H | F | H | CH(CH$_3$)$_2$ | 0.15 (III) | 93 |
| 173 | H | H | phenyl | H | CH(CH$_3$)$_2$ | 0.4 (I) | 86 |
| 174 | H | H | —(CH$_2$)$_3$CH$_3$ | H | —CH$_2$CO$_2$C$_2$H$_5$ | 0.55 | 68.6 |
| 175 | H | H | phenyl | —CH$_2$CO$_2$C$_2$H$_5$ | | | 70.6 |
| 176 | H | H | Br | H | CH$_2$CH$_3$ | 0.133 | 67 |
| 177 | H | H | phenyl | H | CH$_2$CH$_3$ | 0.29 | 66 |
| 178 | H | H | phenyl | H | cyclopropyl | 0.42 | 31 |

TABLE 15-continued

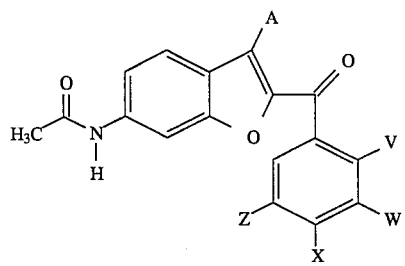

| Example No. | V | W | X | Z | A | $R_f$* | yield (% of theory) |
|---|---|---|---|---|---|---|---|
| 179 | H | H | -C₆H₄-CHO (4-) | H | isopropylidene | 0.22 | 28.4 |
| 180 | H | H | -C₆H₄-CH₂OH (4-) | H | isopropylidene | 0.15 | 89.2 |
| 181 | H | H | C₆H₅ | H | cyclopropyl | 0.32 | 70.9 |
| 182 | H | H | OCH₃ | H | cyclopropyl | 0.29 | 58.4 |
| 183 | OCH₃ | H | OCH₃ | H | cyclopropyl | 0.29 | 67.2 |
| 184 | H | H | Br | H | cyclopropyl | 0.38 | 77.6 |

TABLE 16

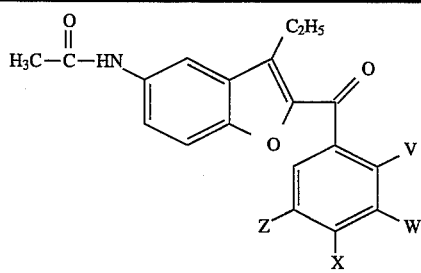

| Example No. | V | W | X | Z | $R_f$* | yield (% of theory) |
|---|---|---|---|---|---|---|
| 185 | Cl | H | Cl | H | 0.51 (I) | 59 |
| 186 | H | CH₃ | H | H | 0.60 (I) | 53 |
| 187 | H | OCH₃ | H | H | 0.43 (I) | 47 |
| 188 | H | CF₃ | H | H | 0.53 (I) | 42 |
| 189 | H | NO₂ | H | H | 0.42 (I) | 12 |
| 190 | H | H | OCH₃ | H | 0.58 | 97 |
| 191 | H | H | C₆H₅ | H | 0.45 | 68 |

TABLE 16-continued

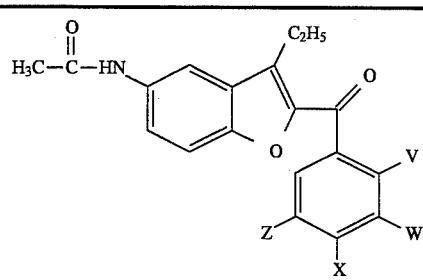

| Example No. | V | W | X | Z | $R_f$* | yield (% of theory) |
|---|---|---|---|---|---|---|
| 192 | H | H | C₂H₅ | H | 0.56 (IV) | 63 |
| 193 | H | H | CH₃ | H | 0.27 (I) | 86 |
| 194 | H | H | cyclohexyl | H | 0.35 (I) | 79 |

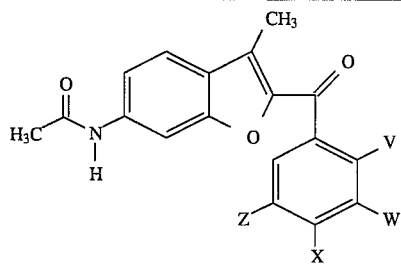
| Example No. | V | W | X | Z | $R_f$* | yield (% of theory) |
|---|---|---|---|---|---|---|
| 195 | H | phenyl | H | H | 0.39 (I) | 65 |
| 196 | H | H | $C_9H_{19}$ | H | 0.06 (III) | 57 |
| 197 | H | H | $C_6H_{13}$ | H | 0.42 (V) | 35 |
| 198 | H | H | 3-pyridyl | H | 0.66 (V) | 67 |
| 199 | H | 3,5-dimethylphenyl | H | H | 0.48 (V) | 83 |
| 200 | H | 3-pyridyl | H | H | 0.68 (V) | 97 |
| 201 | H | H | F | H | 0.8 (I) | 98 |
| 202 | H | H | $C_2H_5$ | H | 0.5 (IV) | 50 |
| 203 | H | H | cyclohexyl | H | 0.6 (IV) | 71 |
| 204 | H | H | $OCH_3$ | H | 0.2 (IV) | 63 |
| 205 | $OCH_3$ | H | $OCH_3$ | H | 0.2 (IV) | 62 |
| 206 | $CH_3$ | H | $CH_3$ | H | 0.4 (I) | 51 |
| 207 | H | H | 4-acetylphenyl | H | 0.2 (I) | 21 |
| 208 | H | phenoxy | H | H | 0.32 (I) | 68 |
| 209 | H | H | OH | H | 0.14 (I) | 20 |
| 210 | H | H | 2-furyl | H | 0.2 (IV) | 61 |
| 211 | H | H | 2-thienyl | H | 0.47 (IV) | 30 |
| 212 | H | H | Br | H | 0.65 | 60 |

-continued
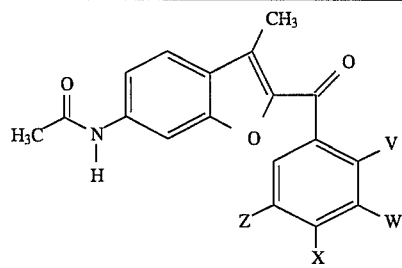
| Example No. | V | W | X | Z | $R_f$* | yield (% of theory) |
|---|---|---|---|---|---|---|
| 213 | H | H | 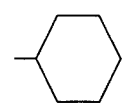 -Cl | H | 0.1 | 76 |
TABLE 18
| Example No. | V | W | X | $R_f$* | yield (% of theory) |
|---|---|---|---|---|---|
| 214 | H | H | F | 0.5 (IV) | 83 |
| 215 | H | H | Br | 0.45 (III) | 68 |
| 216 | H | H | $C_2H_5$ | 0.48 (IV) | 60 |
| 217 | H | H | 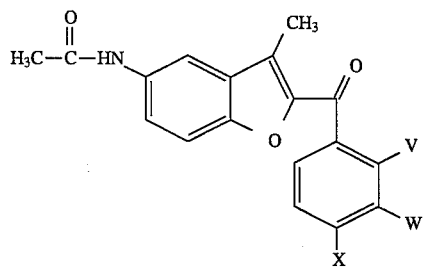 | 0.54 (IV) | 78 |
| 218 | H | Br | H | 0.27 (I) | 71 |
| 219 | Cl | H | Cl | 0.26 (I) | 65 |
| 220 | H | $NO_2$ | H | 0.15 (I) | 20 |
| 221 | H | $CH_3$ | H | 0.25 (I) | 73 |
| 222 | $CH_3$ | H | $CH_3$ | 0.36 (I) | 57 |
| 223 | H | H | $NO_2$ | 0.19 (I) | 16 |
| 224 | H | $CF_3$ | H | 0.35 (I) | 37 |
| 225 | H | $OCH_3$ | H | 0.21 (I) | 96 |
| 226 | H | H | 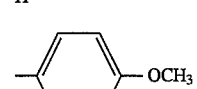-$OCH_3$ | 0.26 (I) | 81 |
TABLE 19
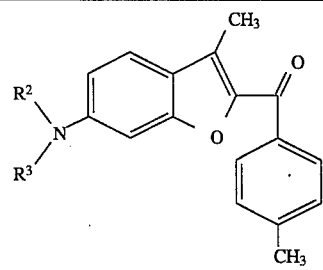
| Example No. | $R^2$ | $R^3$ | $R_f$* | yield (% of theory) |
|---|---|---|---|---|
| 227 | $-CH_2CO_2Et$ | $-CH_2CO_2Et$ | 0.21 (III) | 79 |
| 228 | $-CH_2CO_2H$ | $-CH_2CO_2H$ | 0.03 (II) | 98 |
| 229 | H | $-COCH_2OCH_3$ | 0.6 (II) | 85 |

TABLE 20

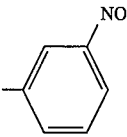

| Example No. | R² | X | W | R_f* | yield (% of theory) |
|---|---|---|---|---|---|
| 230 | —COCH₂OCH₃ | CH₃ | H | 0.6 (III) | 85 |
| 231 | —COCH₃ | H | 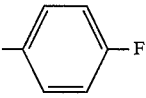 | 0.64 (V) | 55 |
| 232 | —COCH₃ | H | 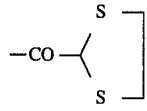 | 0.75 (V) | 31 |
| 233 | —SO₂NHC(CH₃)₃ | CH₃ | H | 0.72 (III) | 58 |
| 234 | —SO₂NH₂ | CH₃ | H | 0.64 (III) | 70 |
| 235 | —COCH₂OCOCH₃ | CH₃ | H | 0.58 (III) | 70 |
| 236 | —COCH₂OH | CH₃ | H | 0.4 (III) | 79 |
| 237 |  | CH₃ | H | | |

The compounds shown in Tables 21 to 24 are prepared in analogy to the abovementioned procedures.

TABLE 21

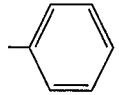

| Ex.-No. | B | X | A | R_f* | yield in % |
|---|---|---|---|---|---|
| 238 | H | CH₃ | 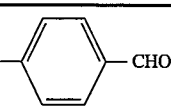 | 0.46 (IV) | 88 |
| 239 | H | CH₃ | —C₂H₅ | 0.35 (IV) | 85 |
| 240 | H | Cl | —CH₂CO₂Et | 0.91 (IV) | 12 |
| 241 | H | 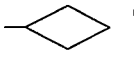 | —C₂H₅ | 0.09 (I) | 63 |

TABLE 21-continued

| Ex.-No. | B | X | A | R_f* | yield in % |
|---|---|---|---|---|---|
| 242 | H | —⟨⟩—CHO | —CH(CH₃)₂ | 0.17 (I) | 28.5 |
| 243 | H | H | 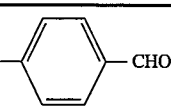 | 0.41 (IV) | 91 |
| 244 | H | CH₃-N⟨⟩ | —CH₃ | 0.34 (IV) | 76 |

TABLE 21-continued

| Ex.-No. | B | X | A | R_f* | yield in % |
|---|---|---|---|---|---|
| 245 | H | Cl | (cyclobutylmethyl) | 0.39 (IV) | 57 |
| 246 | H | —C₂H₅ | (cyclopropyl) | 0.47 (IV) | 73 |
| 247 | H | Cl | —OH | 0.30 (IV) | 52 |
| 248 | H | F | —CH(CH₃)₂ | 0.25 (IV) | 93 |
| 249 | CH₃ | CH₃ | —CH₃ | 0.28 (I) | 53 |

TABLE 22

| Ex.-No. | X | A | R_f* | yield |
|---|---|---|---|---|
| 250 | CH₃ | CH₃ | 0.43 (IV) | 84 |
| 251 | CN | CH₃ | 0.20 (IV) | 42 |
| 252 | H | CH₃ | 0.47 (IV) | 14 |
| 253 | NO₂ | CH₃ | 0.21 (I) | 16 |
| 254 | F | C₂H₅ | 0.44 (IV) | quant. |

TABLE 23

| Ex.-No. | X | A | R_f* | yield (% of theory) |
|---|---|---|---|---|
| 255 | CH₃ | CH₃ | 0.73 (IV) | 97 |
| 256 | H | CH₃ | 0.85 (IV) | 84 |
| 257 | —CN | CH₃ | 0.52 (IV) | 95 |

TABLE 24

| Ex.-No. | R² | A | X | R_f* | yield (% of theory) |
|---|---|---|---|---|---|
| 258 | C₆H₅–CH₂–CH(HNBoc)–C(O)– | isobutyl | Br | 0.65 (IX) | 73 |

TABLE 24-continued

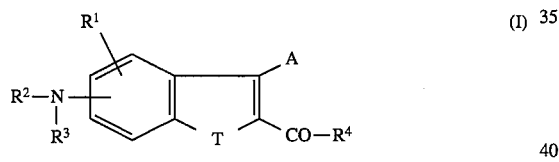

| Ex.-No. | R² | A | X | R_f* | yield (% of theory) |
|---|---|---|---|---|---|
| 259 | C₆H₅—CH(NH₂·HCl)—CO—CH₃ | isopropylidene | Br | 0.68 (X) | 53.8 |
| 260 | C₆H₅—CH(HNBoc)—CO—CH₃ | isopropylidene | phenyl | 0.68 (IX) | 67 |
| 261 | C₆H₅—CH(NH₂·HCl)—CO—CH₃ | isopropylidene | phenyl | 0.66 (X) | 86 |

We claim:

1. An amino-benzofuryl- or thienyl-derivative of the formula

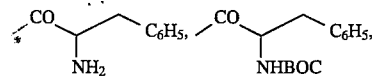

(I)

in which

R¹ represents hydrogen or straight-chain or branched alkyl having up to 6 carbon atoms or represents halogen, carboxyl, cyano, nitro, trifluoromethyl or a group of a formula —OR⁵, —SR⁶ or —NR⁷R⁸, in which R⁵, R⁶ and R⁶ are identical or different and denote hydrogen, cycloalkyl having 3 to 6 carbon atoms, benzyl or a 5 to 7-membered saturated or unsaturated heterocycle having up to 4 hetereoatoms selected from the group consisting of N, S or O and to which a phenyl ring can be fused and which is optionally substituted by identical or different substituents selected from the group consisting of halogen, cyano, nitro or by a straight-chain or branched alkyl having up to 6 carbon atoms or denote straight-chain or branched alkyl or alkenyl each having up to 8 carbon atoms, or denote phenyl, which is optionally monosubstituted to disubstituted by identical or different substituents selected from the group consisting of nitro, halogen, carboxy or straight-chain or branched alkoxycarbonyl having up to 6 carbon atoms, or R⁵ denotes a hydroxyl protecting group, R⁷ denotes hydrogen or a straight-chain or branched alkyl having up to 4 carbon atoms, R² represents formyl or straight-chain or branched acyl, alkoxy or alkoxycarbonyl each having up to 8 carbon atoms in the alkyl group, or represents benzoyl, which is optionally monosubstituted to trisubstituted by identical or different substituents from the series comprising halogen, cyano, carboxy, straight-chain or branched alkoxy, alkoxycarbonyl or acyl each having up to 6 carbon atoms in the alkyl group, or represents a group of a formula

—CO—CH(NH₂)—CH₂—C₆H₅, —CO—CH(NHBOC)—CH₂—C₆H₅,

—SO₂R⁹, —CO—(CH₂)ₐNR¹⁰R¹¹, —CO—(CH₂)ᵦ—R¹², —CO—S—R¹³ or a residue of the formula

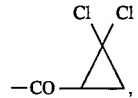

in which

R⁹ denotes straight-chain or branched alkyl having up to 6 carbon atoms, which is optionally substituted by phenyl, or denotes phenyl, which is optionally substituted by trifluoromethyl, cyano, nitro or straight-chain or branched alkyl having up to 6 carbon atoms, R₁₀ and R¹¹ are identical or different and denote hydrogen, straight-chain or branched alkyl having up to 6 carbon atoms or phenyl, R¹² denotes straight-chain or branched hydroxyl, oxyacyl, alloxy or alkoxycarbonyl each having up to 6 carbon atoms or carboxy, a denotes a number 0, 1, 2 or 3, b denotes a number 1, 2 or 3, R¹³ denotes straight-chain or branched alkyl having up to 6 carbon atoms, R³ represents hydrogen or straight-chain or branched alkyl having up to 6 carbon atoms, or has the abovementioned meaning of R², T represents an oxygen or sulfur atom A represents hydrogen, hydroxyl, cycloalkyl with 3 to 6 carbon atoms, carboxy or straight-chain or branched alkoxycarbonyl or alkoxy each having up to 6 carbon atoms, or straight-chain or branched alkyl or alkenyl each having up 8 carbon atoms and each of which is optionally mono-substituted by cyano or by a 5 to 7-membered saturated or unsaturated heterocycle having up to 4 heteroatoms selected from the group consisting of N, S and O, which is optionally substituted by identical or different substituents selected from the group consisting of hydroxy, halogen, cyano, nitro or by a straight-chain or branched alkyl having up to 6 carbon atoms, or alkyl or alkenyl are optionally substituted by a group of a formula

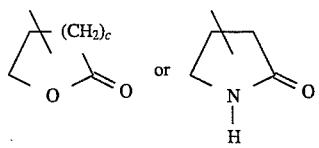

in which c denotes a number 1 or 2, and in which both rings are optionally monosubstituted by hydroxy, halogen or by straight-chain or branched alkyl having up to 6 carbon atoms, or alkyl or alkenyl are optionally monosubstituted by a group of a formula —CO—R¹⁴, —CO—NR¹⁵R¹⁶, —CONR¹⁷—SO₂—R¹⁸ or —PO(OR¹⁹)(OR²⁰), —OR²¹ or

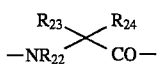

in which

R¹⁴ denotes hydroxyl, cycloalkyloxy having 3 to 7 carbon atoms or straight-chain or branched alkyl or alkoxy each having up to 8 carbon atoms, R¹⁵, R¹⁶ and R¹⁷ are identical or different and represent hydrogen, straight-chain or branched alkyl having up to 6 carbon atoms, phenyl or benzyl, or R¹⁵ denotes hydrogen, and R¹⁶ denotes hydroxyl, or R¹⁵ and R¹⁶ together with the nitrogen atom form a 5- or 6-membered saturated heterocycle, R¹⁸ denotes a straight-chain or branched alkyl having up to 6 carbon atoms, which is optionally substituted by phenyl or trifluoromethyl, or denotes phenyl, which is optionally substituted by substituents from the series comprising halogen, cyano, nitro or by a straight-chain or branched alkyl having up to 6 carbon atoms, R¹⁹, R²⁰ and R²¹ are identical or different and represent hydrogen or straight-chain or branched alkyl having up to 6 carbon atoms, R²² denotes hydrogen, an aminoprotecting group or straight-chain or branched alkyl having up to 6 carbon atoms, R²³ and R²⁴ are identical or different and denote hydrogen or straight-chain or branched alkyl having up to 4 carbon atoms, or R²³ has the abovementioned meaning, and R²⁴ denotes cycloalkyl having 3 to 6 carbon atoms or aryl having 6 to 10 carbon atoms or straight-chain or branched alkyl having up to 8 carbon atoms, which is optionally substituted by cyano, methylthio, hydroxy, mercapto, guanidyl or a group of a formula —NR²⁵R²⁶ or R²⁷—CO—, wherein R²⁵ and R²⁶ have the meaning shown above for R¹⁵, R¹⁶ and R¹⁷, R²⁷ denotes hydroxyl, benzyloxycarbonyl, straight-chain or branched alkoxy having up to 6 carbon atoms or the abovementioned group —NR²⁵R²⁶, alkyl is optionally substituted by cycloalkyl having 3 to 6 carbon atoms, or by aryl having up 6 to 10 carbon atoms, which is optionally substituted by hydroxyl, halogen, nitro, straight-chain or branched alkoxy having up to 8 carbon atoms or by the abovementioned group of the formula —NR²⁵R²⁶, or alkyl is optionally substituted by indolyl wherein the —NH— function is optionally protected by a straight-chain or branched alkyl having up to 6 carbon atoms or by an amino protecting group, or by a 5 to 6 membered unsaturated heterocycle having up to 4 N-atoms wherein all —NH- functions are protected by straight-chain or branched alkyl having up to 6 carbon atoms or by an amino protecting group, and R⁴ represents phenyl, which is optionally monosubstituted to trisubstituted by identical or different substituents selected from the group consisting of hydroxyl, adamantyl, phenoxy, cycloalkyl having up to 3 to 6 carbon atoms, halogen, nitro, furanyl, thienyl, pyridyl, tetrazolyl, trifluoromethyl, difluoromethyl, cyano, carboxyl, straight-chain or branched alkyl, alkoxy, alkoxycarbonyl or acyl each having up to 11 carbon atoms in the alkyl group or by phenyl, which is optionally monosubstituted to trisubstituted by nitro, halogen, formyl, carbonyl or straight-chain or branched alkoxy, acyl, alkoxycarbonyl or alkyl each having up to 6 carbon atoms, which is optionally substituted by hydroxyl or phenyl is substituted by a group of formula —NR²⁸R²⁹, —SR³⁰, SO₂R³¹, —O—SO₂R³² or

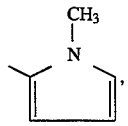

in which

R²⁸ and R²⁹ have the meaning shown above for R¹⁰ and R¹¹, or

R²⁸ denotes hydrogen, and

R²⁹ denotes straight-chain or branched acyl having up to 6 carbon atoms,

R³⁰ denotes straight-chain or branched alkyl having up to 6 carbon atoms,

R³¹ and R³² are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, with the proviso that A does not denote methyl or

II if A represents a methyl group R¹, T and R⁴ have the meaning described in part I, and in this case $R^2$ and $R^3$ are identical or different and represent hydrogen or straight-chain or branched alkyl having up to 6 carbon atoms, or represent formyl or straight-chain or branched acyl, alkoxy or alkoxy carbonyl each having up to 8 carbon atoms, or represent benzoyl, which is optionally monosubstituted to trisubstituted by identical or different substituents selected from the group consisting of halogen, cyano, carboxy, straight-chain or branched alkoxy, alkoxycarbonyl or acyl each having up to 6 carbon atoms, or represent a group of a formula $-SO_2(NH)_gR^{33}$, $SO_2NH_2$, $-CO-(CH_2)_dNR^{34}R^{35}$, $-(CH_2)_e-CO-R^{36}$, $-CO-(CH_2)_f-R^{37}$ or $-CO-X$, in which $R^{33}$ has the abovementioned meaning of $R^9$ and is identical or different to the latter, $R^{34}$ and $R^{35}$ are identical or different and have the abovementioned meaning of $R^{10}$ and $R^{11}$, $R^{36}$ denotes hydroxyl or straight-chain or branched alkoxy having up to 6 carbon atoms, $R^{37}$ has the abovementioned meaning of $R^{12}$ or denotes straight-chain or branched alkoxy or oxyacyl each having up to 6 carbon atoms or hydroxyl, d has the abovementioned meaning of a, e denotes a number 1, 2, 3, 4 or 5, f has the abovementioned meaning of b, g denotes a number 0 or 1, X denotes a 5-membered saturated or unsaturated heterocycle having up to 3 heteroatoms selected from the group consisting of N, S or O, which is optionally monosubstituted to trisubstituted by nitro, methyl or ethyl, or X denotes a residue of the formula

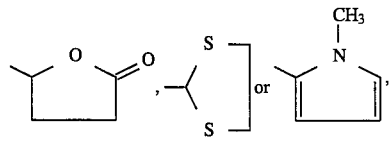

or

III $R^1$, A and T have the abovementioned meaning described in part I or

A represents methyl, $R^2$ and $R^3$ have the abovementioned meaning described in part II, and in this case $R^4$ represents a 5 to 7 membered, saturated or unsaturated hetereocycle, which contains up to three oxygen, sulphur and/or nitrogen atoms as heteroatoms and to which further a benzene ring can be fused and wherein both rings are optionally monosubstituted to trisubstituted by identical or different substituents selected from the group consisting of hydroxyl, halogen, nitro, 1H-tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 8 carbon atoms or by a group of formula $-NR^{38}R^{39}$, $-SR^{40}$, $SO_2R^{41}$ or $-O-SO_2R^{42}$, in which $R^{38}$ and $R^{39}$ have the meaning shown above for $R^{28}$ and $R^{29}$ and are identical to the latter or different from the latter, $R^{40}$ has the abovementioned meaning of $R^{30}$, $R^{41}$ and $R^{42}$ are identical or different and have the abovementioned meaning of $R^{31}$ and $R^{32}$, or a salt thereof, provided that N-[2-(4-ethoxybenzoyl)-3-hydroxy-5-benzofuranyl]-acetamide; 6-amino-2-benzoyl-5-cyano-3-methylbenzofuran; 6-amino-2-(4-p-chlorobenzoyl)-5-cyano-3-methylbenzofuran; N-[2-benzoyl)-3-methyl-5-benzofuranyl]-acetamide; N-[2-(2,5-dimethylbenzoyl)-3-methyl-5-benzofuranyl]-acetamide; and 5-amino-2-benzoyl-3-methylbenzofuran and salts thereof are excluded.

2. An amino-benzofuryl- or thienyl-derivative according to claim 1, wherein

I $R^1$ represents hydrogen, straight-chain or branched alkyl having up to 4 carbon atoms or represents fluorine, chlorine, bromine, nitro, trifluoromethyl or a group of a formula $-OR^5$, $-SR^6$ or $-NR^7R^8$, in which $R^7$ denotes hydrogen or a straight-chain or branched alkyl having up to 3 carbon atoms, $R^5$, $R^6$ and $R^8$ are identical or different and denote hydrogen, cyclopropyl, cyclopentyl, cyclohexyl, chinolyl, pyridyl, imidazolyl, 1,3-thiazolyl or thienyl, which are optionally substituted by identical or different substituents selected from the group consisting of fluorine, chlorine, bromine, iodine, cyano, nitro or by a straight-chain or branched alkyl having up to 5 carbon atoms, or denote straight-chain or branched alkyl or alkenyl each having up to 6 carbon atoms, or denote phenyl, which is optionally monosubstituted to disubstituted by identical or different substituents selected from the group consisting of nitro, fluorine, chlorine, bromine, iodine, carboxy or straight-chain or branched alkoxycarbonyl having up to 5 carbon atoms, or $R^5$ denotes benzyl, acetyl or tetrahydropyranyl, $R^2$ represents formyl or straight-chain or branched acyl, alkoxy or alkoxy carbonyl each having up to 6 carbon atoms in the alkyl group, or represents benzoyl, which is optinally monosubstituted by substituents selected from the group consisting of fluorine, chlorine, bromine, cyano, carboxy, straight-chain or branched alkoxy, alkoxycarbonyl or acyl each having up to 4 carbon atoms in the alkyl group, or represents a group of a formula

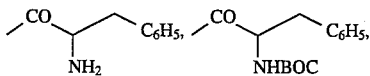

$-SO_2R^9$, $-CO-(CH_2)_aNR^{10}R^{11}$, $-CO-(CH_2)_b-R^{12}$, $-CO-S-R^{13}$ or a residue of the formula

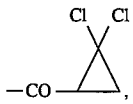

in which $R^9$ denotes straight-chain or branched alkyl having up to 4 carbon atoms, which is optionally substituted by phenyl, or denotes phenyl, which is optionally substituted by trifluoromethyl, cyano, nitro or straight-chain or branched alkyl having up to 4 carbon atoms, $R^{10}$ and $R^{11}$ are identical or different and denote hydrogen, straight-chain or branched alkyl having up to 4 carbon atoms or phenyl, $R^{12}$ denotes straight-chain or branched alkoxycarbonyl having up to 4 carbon atoms or carboxy, a denotes a number 0, 1, 2 or 3, b denotes a number 1, 2 or 3, $R^{13}$ denotes straight-chain or branched alkyl having up to 4 carbon atoms, $R^3$ represents hydrogen or straight-chain or branched alkyl having up to 4 carbon atoms, or has the abovementioned meaning of $R^2$, T represents an oxygen atom A represents hydrogen, hydroxyl, cyclopropyl, cyclobutyl, cyclopentyl, carboxyl or straight-chain or a branched alkoxycarbonyl or alkoxy each having up to 4 carbon atoms, or straight-chain or branched alkyl or alkenyl each having up to 6 carbon atoms and each of which is optionally monosubstituted by cyano, tetrazolyl, oxazolyl, oxazolinyl, thiazolyl or a group of a formula

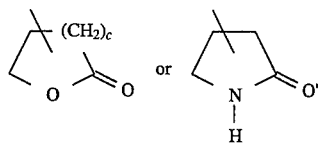

in which c denotes a number 1 or 2 and in which all rings are optionally monosubstituted by hydroxy, fluorine, bromine, chlorine or by straight-chain or branched alkyl having up to 4 carbon atoms, or alkyl or alkenyl are optionally monosubstituted by a group of a formula —CO—$R^{14}$, —CO—$NR^{15}R^{16}$ or —$OR^{21}$, in which $R^{14}$ denotes hydroxyl, cyclopropyloxy, cyclopentyloxy, cyclohexyloxy or straight-chain or branched alkyl or alkoxy each having up to 6 carbon atoms, $R^{15}$ and $R^{16}$ are identical or different and represent hydrogen, straight-chain or branched alkyl having up to 4 carbon atoms, phenyl or benzyl, or $R^{15}$ denotes hydrogen, and $R^{16}$ denotes hydroxyl, or $R^{15}$ and $R^{16}$ together with the nitrogen atom form a pyrrolidinyl, morpholinyl or a piperidinyl ring, $R^{21}$ represents hydrogen or straight-chain or branched alkyl having up to 6 carbon atoms, and $R^4$ represents phenyl, which is optionally monosubstituted to trisubstituted by identical or different substituents selected from the group consisting of hydroxyl, adamantyl, phenoxy, cyclopropyl, cyclopentyl, cyclohexyl, fluorine, chlorine, bromine, iodine, nitro, tetrazolyl, furanyl, thienyl, pyridyl, trifluoromethyl, difluoromethyl, cyano, carboxy, straight-chain or branched alkyl, alkoxy, alkoxycarbonyl or acyl each having up to 10 carbon atoms in the alkyl group, or by phenyl, which is optionally monosubstituted to tribsubstituted by fluorine, chlorine, bromine, nitso, formyl or straight-chain or branched alkoxy, acyl, ethoxycarbonyl or alkyl each having up to 4 carbon atoms, which is optionally substituted by hydroxyl, or phenyl is substituted by a group of formula —$NR^{28}R^{29}$, —$SR^{30}$, —$SO_2R^{31}$, —O—$SO_2R^{32}$ or

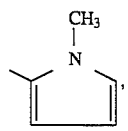

in which $R^{28}$ and $R^{29}$ have the meaning shown above for $R^{10}$ and $R^{11}$, or $R^{28}$ denotes hydrogen, and $R^{29}$ denotes straight-chain or branched acyl having up to 6 carbon atoms, $R^{30}$ denotes straight-chain or branched alkyl having up to 4 carbon atoms, $R^{31}$ and $R^{32}$ are identical or different and represent straight-chain or branched alkyl having up to 5 carbon atoms or phenyl, which is optionally substituted by trifluoromethyl, fluorine, chlorine, bromine or straight-chain or branched alkyl having up to 3 carbon atoms, with the proviso that A does not denote methyl, or

II if A represents a methyl group $R^1$, T and $R^4$ have the abovementioned meaning described in part I, and in this case $R^2$ and $R^3$ are identical or different and represent hydrogen or straight-chain or branched alkyl having up to 4 carbon atoms, or or represent benzoyl, which is optionally substituted by substituents selected from the group consisting of fluorine, chlorine, bromine, cyano, carboxy, straight-chain or branched alkoxy, alkoxycarbonyl or acyl each having up to 4 carbon atoms, or represent a group of a formula —$SO_2$—$(NH)_g$—$R^{33}$, $SO_2NH_2$, —CO—$(CH_2)_d$—$NR^{34}R^{35}$, —$(CH_2)_e$—CO—$R^{36}$, —CO—$(CH_2)_f$—$R^{37}$ or CO—X, in which $R^{33}$ has the abovementioned meaning of $R^9$ and is identical or different to the latter, $R^{34}$ and $R^{35}$ are identical or different and denote hydrogen or methyl, $R^{36}$ denotes hydroxyl or straight-chain or branched alkoxy having up to 4 carbon atoms or carboxy, $R^{37}$ has the abovementioned meaning of $R^{12}$ or denotes hydroxyl or straight-chain or branched alkoxy or oxacyl each having up to 4 carbon atoms, d has the abovementioned meaning of a, e denotes a number 1, 2, 3 or 4, f has the abovementioned meaning of c, g denotes a number 0 or 1, X denotes pyrrolyl, furyl or isoxazolyl, which are optionally mono-substituted to trisubstituted by nitro, methyl or ethyl or X denotes a residue of the formula

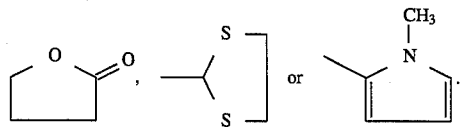

or

III $R^1$, A and T have the meaning described in part I, or

A represents methyl, $R^2$ and $R^3$ have the meaning described in part II and in this case $R^4$ represents pyridyl, imidazolyl, pyrazolyl, thienyl, isothiazolyl, 1,3-thiazolyl or benzothiophenyl, where all rings are optionally monosubstituted to trisubstituted by identical or different substituents selected from the group consisting of hydroxyl, fluorine, chlorine, bromine, iodine, nitro, 1H-tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 6 carbon atoms or by a group of formula —$NR^{38}R^{39}$, $SR^{40}$, —$SO_2R^{41}$ or —O—$SO_2R^{42}$, in which $R^{38}$ and $R^{39}$ have the meaning shown above for $R^{28}$ and $R^{29}$ and are identical to the latter or different from the latter, $R^{40}$ has the abovementioned meaning of $R^{30}$, $R^{41}$ and $R^{42}$ are identical or different and have the abovementioned meaning of $R^{31}$ and $R^{32}$, or a salt thereof.

3. A amino-benzofuryl- or thienyl-derivative according to claim 1, wherein

I $R^1$ represents hydrogen, straight-chain or branched alkyl having up to 3 carbon atoms, fluorine, chlorine, bromine, nitro or trifluoromethyl, $R^2$ represents formyl or straight-chain or branched acyl, or alkoxycarbonyl each having up to 5 carbon atoms in the alkyl group, or represents benzoyl, which is optionally substituted by substituents selected from the group consisting of fluorine, chlorine, bromine, cyano, carboxy, straight-chain or branched alkoxy, alkoxycarbonyl or acyl, each having up to 3 carbon atoms in the alkyl group, or represents a group of a formula

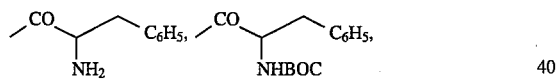

—$SO_2R^9$, —CO—$(CH_2)_aNR^{10}R^{11}$, —CO—$(CH_2)_b$—$R^{12}$, —CO—S—$R^{13}$ or a residue of the formula

in which $R^9$ denotes straight-chain or branched alkyl having up to 4 carbon atoms, which is optionally substituted by phenyl, or denotes phenyl, which is optionally substituted by trifluoromethyl, cyano or straight-chain or branched alkyl having up to 3 carbon atoms, $R^{10}$ and $R^{11}$ are identical or different and denote hydrogen, straight-chain or branched alkyl having up to 3 carbon atoms or phenyl, $R^{12}$ denotes straight-chain or branched alkoxycarbonyl having up to 3 carbon atoms or carboxy, a denotes a number 0, 1, 2 or 3, b denotes a number 1, 2 or 3, $R^{13}$ denotes straight-chain or branched alkyl having up to 3 carbon atoms, $R^3$ represents hydrogen or straight-chain or branched alkyl having up to 3 carbon atoms, or has the abovementioned meaning of $R^2$, T represents an oxygen or sulfur atom, A represents hydrogen, hydroxyl, cyclopropyl, cyclobutyl, cyclopentyl, carboxyl, or straight-chain or a branched alkoxycarbonyl or alkoxy each having up to 3 carbon atoms, or straight-chain or branched alkyl having up to 5 carbon atoms which is optionally monosubstituted by cyano or by a group of a formula —CO—$R^{14}$, —CO—$NR^{15}R^{16}$, in which $R^{14}$ denotes hydroxyl, cyclopropyloxy, cyclopentyloxy, cyclohexyloxy or straight-chain or branched alkyl or alkoxy having up to 5 carbon atoms, $R^{15}$ and $R^{16}$ are identical or different and denote hydrogen, straight-chain or branched alkyl having up to 3 carbon atoms or phenyl, and $R^4$ represents phenyl, which is optionally monosubstituted to trisubstituted by identical or different substituents selected from the group consisting of hydroxyl, adamantyl, phenoxy, N-methyl-pyrrolyl, cyclopropyl, cyclopentyl, cyclohexyl, fluorine, chlorine, bromine, furanyl, thienyl, pyridyl, nitro, trifluoromethyl, difluoromethyl, cyano, carboxyl, methylthio, straight-chain or branched alkyl, alkoxy, acyl or alkoxycarbonyl each having up to 9 carbon atoms, or by phenyl, which is optionally monosubstituted to trisubstituted by fluorine, chlorine, bromine, nitro, formyl or straight-chain or branched alkoxy, alkoxycarbonyl, acyl or alkyl each having up to 4 carbon atoms, which is optionally substituted by hydroxyl, with the proviso that A does not denote methyl, or

II if A represents a methyl group, $R^1$, T and $R^4$ have the meaning described in part I, and in this case $R^2$ and $R^3$ are identical or different and represent hydrogen or straight-chain or branched alkyl having up to 3 carbon atoms, or represent formyl or straight-chain or branched acyl or alkoxycarbonyl each having up to 4 carbon atoms, or represent benzoyl, which is optionally substituted by substituents from the series comprising fluorine, chlorine, bromine, cyano, straight-chain or branched alkoxy or alkoxycarbonyl each having up to 3 carbon atoms, or represent a group of a formula —CO—$NH_2$, —$SO_2(NH)_gR^{33}$, —$SO_2NH_2$, —$(CH_2)_e$—CO—$R^{36}$, —CO—$(CH_2)_f$—$R^{37}$ or —CO—X, in which $R^{33}$ has the abovementioned meaning of $R^9$ and is identical or different to the latter, $R^{37}$ has the abovementioned meaning of $R^{12}$ or denotes hydroxyl or straight-chain or branched alkoxy or oxacyl each having up to 4 carbon atoms, $R^{36}$ denotes hydroxyl or straight-chain or branched alkoxy having up to 3 carbon atoms, d has the abovementioned meaning of a, f has the abovementioned meaning of b, g denotes a number 0 or 1, X denotes pyrrolyl, N-methyl-pyrrolyl, furyl or isoxacolyl, which are optionally monosubstituted to trisubstituted by nitro, methyl or ethyl, or X denotes a residue of the formula

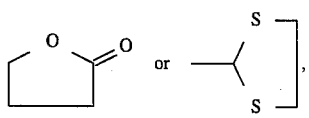

b denotes a number 1 or 2, or

III $R^1$, A and T have the abovementioned meaning described in part I, or

A represents methyl, $R^2$ and $R^3$ have the meaning described in part II, and in this case $R^4$ represents pyridyl, which optionally is up to substituted to trisubstituted by identical or different substituents selected from the group consisting of hydroxyl, fluorine, chlorine, bromine, nitro, trifluoromethyl, trifluoromethoxy, difluoromethyl, difluoromethoxy, cyano, carboxy, straight-chain or branched alkyl, alkoxy, alkoxycarbonyl or acyl each having up to 5 carbon atoms or a salt thereof.

4. An amino-benzofuryl or thienyl-derivative according to claim 1, wherein

I $R^1$ represents hydrogen, $R^2$ represents formyl or methyl or represents benzoyl, which is optionally substituted by substituents selected from the group consisting of fluorine, chlorine, bromine, cyano, carboxy, straight-chain or branched alkoxy, alkoxycarbonyl or acyl, each having up to 3 carbon atoms in the alkyl group, or represents a group of a formula

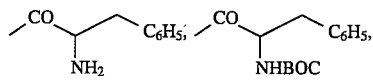

$-SO_2R^9$, $-CO-(CH_2)_aNR^{10}R^{11}$, $-CO-(CH_2)_b-R^{12}$, $-CO-S-R^{13}$ or a residue of the formula

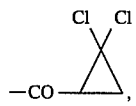

in which $R^9$ denotes straight-chain or branched alkyl having up to 4 carbon atoms, $R^{10}$ and $R^{11}$ are identical or different and denote hydrogen, straight-chain or branched alkyl having up to 3 carbon atoms or phenyl, $R^{12}$ denotes straight-chain or branched alkoxycarbonyl having up to 3 carbon atoms or carboxy, a denotes a number 0, 1, 2 or 3, b denotes a number 1, 2 or 3, $R^{13}$ denotes straight-chain or branched alkyl having up to 3 carbon atoms, $R^3$ represents hydrogen or straight-chain or branched alkyl having up to 3 carbon atoms, or has the abovementioned meaning of $R^2$, T represents an oxygen or sulfur atom, A represents hydrogen, hydroxyl, cyclopropyl, cyclobutyl, cyclopentyl, carboxyl, or straight-chain or a branched alkoxycarbonyl or alkoxy each having up to 3 carbon atoms, or straight-chain or branched alkyl having up to 5 carbon atoms which is optionally monosubstituted by cyano or by a group of a formula $-CO-R^{14}$, $-CO-NR^{15}R^{16}$, in which $R^{14}$ denotes hydroxyl, cyclopropyloxy, cyclopentyloxy, cyclohexyloxy or straight-chain or branched alkyl or alkoxy having up to 5 carbon atoms, $R^{15}$ and $R^{16}$ are identical or different and denote hydrogen, straight-chain or branched alkyl having up to 3 carbon atoms or phenyl, and $R^4$ represents phenyl, which is optionally monosubstituted to trisubstituted by identical or different substituents selected from the group consisting of hydroxyl, adamantyl, phenoxy, N-methyl-pyrrolyl, cyclopropyl, cyclopentyl, cyclohexyl, fluorine, chlorine, bromine, furanyl, thienyl, pyridyl, nitro, trifluoromethyl, difluoromethyl, cyano, carboxyl, methylthio, straight-chain or branched alkyl, alkoxy, acyl or alkoxycarbonyl each having up to 9 carbon atoms, or by phenyl, which is optionally monosubstituted to trisubstituted by fluorine, formyl or straight-chain or branched-alkyl having up to 3 carbon atoms, which is optionally substituted by hydroxyl, with the proviso that A does not denote methyl, or

II if A represents a methyl group, $R^1$, T and $R^4$ have the meaning described in part I, and in this case $R^2$ and $R^3$ are identical or different and represent hydrogen or straight-chain or branched alkyl having up to 3 carbon atoms, or represent formyl or straight-chain or branched acyl or alkoxycarbonyl each having up to 4 carbon atoms, or represent benzoyl, which is optionally substituted by substituents selected from the group consisting of fluorine, chlorine, bromine, cyano, straight-chain or branched alkoxy or alkoxycarbonyl each having up to 3 carbon atoms, or represent a group of a formula $-CO-NH_2$, $-SO_2(NH)_gR^{33}$, $-SO_2NH_2$, $-(CH_2)_e-CO-R^{36}$, $-CO-(CH_2)_f-R^{37}$ or $-CO-X$, in which $R^{33}$ has the abovementioned meaning of $R^9$ and is identical or different to the latter, $R^{37}$ has the abovementioned meaning of $R^{12}$ or denotes hydroxyl or straight-chain or branched alkoxy or oxacyl each having up to 4 carbon atoms, $R^{36}$ denotes hydroxyl or straight-chain or branched alkoxy having up to 3 carbon atoms, e denotes a number 1, 2, 3 or 4, f has the abovementioned meaning of b, g denotes a number 0 or 1, X denotes pyrrolyl, N-methyl-pyrrolyl, furyl or isoxacolyl, which are optionally monosubstituted to trisubstituted by nitro, methyl or ethyl, or X denotes a residue of the formula

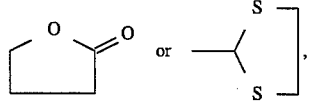

b denotes a number 1 or 2, or

III $R^1$, A and T have the abovementioned meaning described in part I, or

A represents methyl, $R^2$ and $R^3$ have the meaning described in part II, and in this case $R^4$ represents pyridyl, which optionally is optionally substituted to trisubstituted by identical or different substituents from the group consisting of hydroxyl, fluorine, chlorine, bromine, nitro, trifluoromethyl, trifluoromethoxy, difluoromethyl, difluoromethoxy, cyano, carboxy, straight-chain or branched alkyl, alkoxy, alkoxycarbonyl or acyl each having up to 5 carbon atoms, or a salt thereof.

5. An amino-benzofuryl or thienyl-derivative of the formula $$\underset{R^3}{\underset{|}{R^2-N}}\underset{T}{\overset{R^1}{\diagdown}}\overset{A}{\diagup}CO-R^4 \quad (I)$$

wherein

I $R^1$ represents hydrogen, $R^2$ represents formyl or methyl or represents benzoyl, which is optionally substituted by substituents selected from the group consisting of fluorine, chlorine, bromine, cyano, carboxy, straight-chain or branched alkoxy, alkoxycarbonyl or acyl, each having up to 3 carbon atoms in the alkyl group, or represents a group of a formula $$\underset{NH_2}{\overset{CO}{\diagup}}C_6H_5, \quad \underset{NHBOC}{\overset{CO}{\diagup}}C_6H_5,$$

$-SO_2R^9$, $-CO-(CH_2)_aNR^{10}R^{11}$, $-CO-(CH_2)_b-R^{12}$, $-CO-S-R^{13}$ or a residue of the formula $$-CO-\underset{}{\overset{Cl\quad Cl}{\triangle}},$$

in which $R^9$ denotes straight-chain or branched alkyl having up to 4 carbon atoms, $R^{10}$ and $R^{11}$ are identical or different and denote hydrogen, straight-chain or branched alkyl having up to 3 carbon atoms or phenyl, $R^{12}$ denotes straight-chain or branched alkoxycarbonyl having up to 3 carbon atoms or carboxy, a denotes a number 0, 1, 2 or 3, b denotes a number 1, 2 or 3, $R^{13}$ denotes straight-chain or branched alkyl having up to 3 carbon atoms, $R^3$ represents hydrogen or straight-chain or branched alkyl having up to 3 carbon atoms, or has the abovementioned meaning of $R^2$, T represents an oxygen or a sulfur atom, A represents hydrogen, cyclopropyl, cyclobutyl, cyclopentyl, carboxyl, or straight-chain or a branched alkoxycarbonyl or alkoxy each having up to 3 carbon atoms, or straight-chain or branched alkyl having up to 5 carbon atoms which is optionally monosubstituted by cyano or by a group of a formula $-CO-R^{14}$, $-CO-NR^{15}R^{16}$, in which $R^{14}$ denotes hydroxyl, cyclopropyloxy, cyclopentyloxy, cyclohexyloxy or straight-chain or branched alkyl or alkoxy having up to 5 carbon atoms, $R^{15}$ and $R^{16}$ are identical or different and denote hydrogen, straight-chain or branched alkyl having up to 3 carbon atoms or phenyl, and $R^4$ represents phenyl, which is optionally monosubstituted to trisubstituted by identical or different substituents selected from the group consisting of hydroxyl, adamantyl, phenoxy, N-methyl-pyrrolyl, cyclopropyl, cyclopentyl, cyclohexyl, fluorine, chlorine, bromine, furanyl, thienyl, pyridyl, nitro, trifluoromethyl, difluoromethyl, cyano, carboxyl, methylthio, straight-chain or branched alkyl, alkoxy, acyl or alkoxycarbonyl each having up to 9 carbon atoms, or by phenyl, which is optionally monosubstituted to trisubstituted by fluorine formyl or straight-chain or branched-alkyl having up to 3 carbon atoms, which is optionally substituted by hydroxyl, with the proviso that A does not denote methyl, or when A represents hydroxyl $R^4$ represents phenyl, which is optionally monosubstituted to trisubstituted by identical or different substituents selected from the group consisting of hydroxyl, adamantyl, phenoxy, N-methyl-pyrrolyl, cyclopropyl, cyclohexyl, fluorine, chlorine, bromine, furanyl, thienyl, pyridyl, nitro, trifluoromethyl, difluoromethyl, cyano, carboxyl, methylthio, straight-chain or branched alkyl, alkoxy, acyl or alkoxycarbonyl each having up to 9 carbon atoms, or by phenyl, which is optionally monosubstituted to trisubstituted by fluorine, formyl or straight-chain or branched alkyl having up to 3 carbon atoms, which is optionally substituted by hydroxyl,

II if A represents a methyl group, $R^1$ and T have the meaning described in part I, and in this case $R^2$ and $R^3$ are identical or different and represent hydrogen or straight-chain or branched alkyl having up to 3 carbon atoms, or represent formyl or straight-chain or branched acyl or alkoxycarbonyl each having up to 4 carbon atoms or represent benzoyl, which is optionally substituted by substituents selected from the group consisting of fluorine, chlorine, bromine, cyano, straight-chain or branched alkoxy or alkoxycarbonyl each having up to 3 carbon atoms, or represents a group of a formula $-CO-NH_2$, $SO_2NH_2$, $-(CH_2)_e-CO-R^{36}$, $-CO-(CH_2)_f-R^{37}$ or $-CO-X$, in which $R^{37}$ has the abovementioned meaning of $R^{12}$ or denotes hydroxyl or straight-chain or branched alkoxy or oxacyl each having up to 4 carbon atoms, $R^{36}$ denotes hydroxyl or straight-chain or branched alkoxy having up to 3 carbon atoms, e denotes a number 1, 2, 3 or 4, f has the abovementioned meaning of b, X denotes pyrrolyl, N-methyl-pyrrolyl, furyl or isoxacolyl, which are optionally monosubstituted to trisubstituted by nitro, methyl or ethyl, or X denotes a residue of the formula

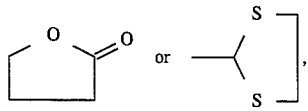

b denotes a number 1 or 2, and $R^4$ represents phenyl, which is optionally monosubstituted to trisubstituted by identical or different substituents selected from the group consisting of hydroxyl, adamantyl, phenoxy, N-methyl-pyrrolyl, cyclopropyl, cyclopentyl, cyclohexyl, fluorine, chlorine, bromine, furanyl, thienyl, pyridyl, nitro, trifluoromethyl, difluoromethyl, cyano, carboxyl, methylthio, straight-chain or branched acyl or alkoxycarbonyl each having up to 9 carbon atoms, or by phenyl, which is optionally monosubstituted to trisubstituted by fluorine, formyl or straight-chain or branched-alkyl having up to 3 carbon atoms, which is optionally substituted by hydroxyl,

III if A represents methyl, $R^1$, A and T have the abovementioned meaning described in part I, $R^2$ and $R^3$ have the meaning described in part II, and in this case $R^4$ represents pyridyl, which optionally is optionally substituted to trisubstituted by identical or different substituents from the group consisting of hydroxyl, fluorine, chlorine, bromine, nitro, trifluoromethyl, trifluoromethoxy, difluoromethyl, difluoromethoxy, cyano, carboxy, straight-chain or branched alkyl, alkoxy, alkoxycarbonyl or acyl each having up to 5 carbon atoms, or a salt thereof.

6. A compound according to claim 1 wherein such compound is N-[3-methyl-2-(4-methyl-benzoyl)-benzofuran-6-yl]-acetamide of the formula

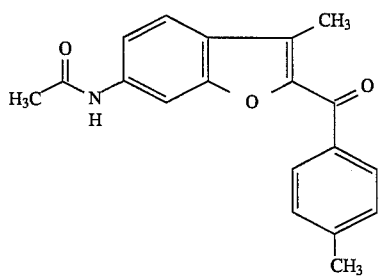

or a salt thereof.

7. A compound according to claim 1 wherein such compount is N-[3-ethyl-2-(4-methyl-benzoyl)-benzofuran-5-yl]-acetamide of the formula

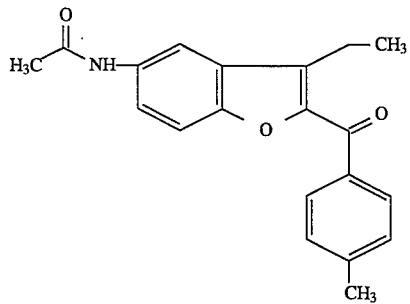

or a salt thereof.

8. A compound wherein such compount is [3-methyl-2-(4-methyl-benzoyl)-benzofuran-6-ylamino]-acetic acid ethyl ester of the formula

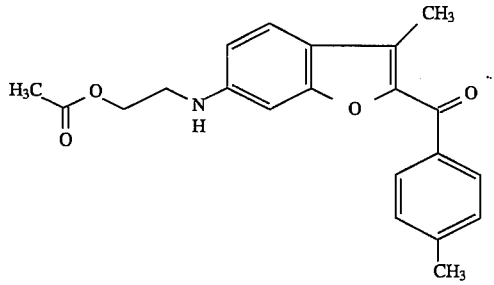

or a salt thereof.

9. A compound according to claim 1 wherein such compound is N-[3-(2-methoxycarbonyl-ethyl)-2-(4-methyl-benzoyl)-benzofuran-6-yl]-malonamic acid methyl ester of the formula

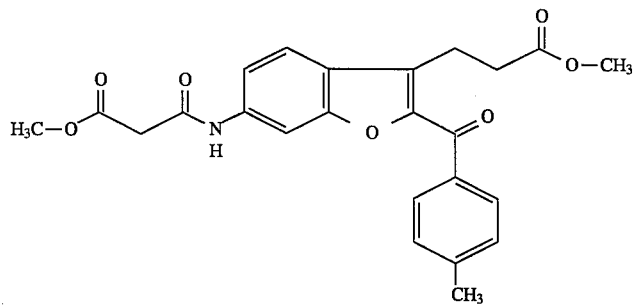

or a salt thereof.

10. A compound according to claim 1 wherein such compount is 2-methoxy-N-[3-methyl-2-(4-methyl-benzoyl)-benzofuran-6-yl]-acetamide of the formula

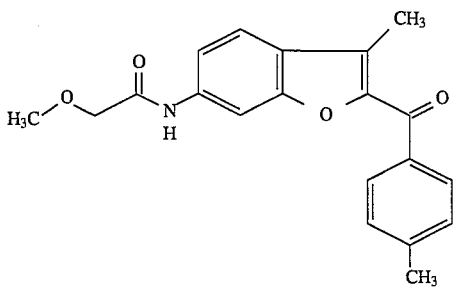

or a salt thereof.

11. A composition for the treatment of acute and chronic inflammatory processes comprising an amount effective therefore of a compound or salt thereof according to claim 1 and a pharmacologically acceptable diluent.

12. The method of treating acute and chronic inflammatory processes in a patient in need thereof which comprises administering to such patient an amount effective therefor of a compound or salt thereof according to claim 1.

13. A composition for the treatment of acute and chronic inflammatory processes comprising an amount effective therefore of a compound or salt thereof according to claim 8 and a pharmacologically acceptable diluent.

14. The method of treating acute and chronic inflammatory processes in a patient in need thereof which comprises administering to such patient an amount effective therefor of a compound or salt thereof according to claim 8.

* * * * *

UNITED STATES PATENT AND TRADEMARK OFFICE
CERTIFICATE OF CORRECTION

PATENT NO. : 5,622,989
DATED : April 22, 1997
INVENTOR(S) : Braunlich, et al.

It is certified that error appears in the above-indentified patent and that said Letters Patent is hereby corrected as shown below:

Col. 58, line 13    Before " alkyl " insert -- or --

Col. 61, line 62    Delete " nitso " and substitute -- nitro --

Col. 63, line 4     Delete " benzothiophenyl " and substitute -- benzo[b]thiophenyl --

Signed and Sealed this

Fourth Day of November, 1997

Attest:

BRUCE LEHMAN

*Attesting Officer*    *Commissioner of Patents and Trademarks*